(12) United States Patent
Herrmann et al.

(10) Patent No.: US 10,987,428 B2
(45) Date of Patent: Apr. 27, 2021

(54) PHOSPHOROTHIOATE-CONJUGATED MIRNAS AND METHODS OF USING THE SAME

(71) Applicant: City of Hope, Duarte, CA (US)

(72) Inventors: Andreas Herrmann, Del Mar, CA (US); Hua Yu, Glendora, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 16/430,327

(22) Filed: Jun. 3, 2019

(65) Prior Publication Data

US 2019/0365905 A1 Dec. 5, 2019

Related U.S. Application Data

(60) Provisional application No. 62/679,596, filed on Jun. 1, 2018.

(51) Int. Cl.
*A61K 48/00* (2006.01)
*C07H 21/04* (2006.01)
*A61K 47/54* (2017.01)

(52) U.S. Cl.
CPC .......... *A61K 47/549* (2017.08); *A61K 47/548* (2017.08)

(58) Field of Classification Search
CPC ............ C12N 15/113; C12N 2310/141; A61K 31/713
See application file for complete search history.

(56) References Cited

U.S. PATENT DOCUMENTS

| 5,034,506 A | 7/1991 | Summerton et al. |
| 5,235,033 A | 8/1993 | Summerton et al. |
| 8,852,940 B2 * | 10/2014 | Blelloch .............. A61K 35/545 424/93.7 |
| 10,023,868 B2 * | 7/2018 | Weijzen ............... C12N 15/113 |
| 10,125,398 B2 * | 11/2018 | Grillari ............... C12Q 1/6883 |
| 10,336,829 B2 * | 7/2019 | Fu ...................... C07K 16/2818 |
| 10,351,849 B2 * | 7/2019 | Lee ..................... A61K 31/7105 |
| 2012/0259001 A1 * | 10/2012 | Khvorova ............ C12N 15/111 514/44 A |
| 2016/0015824 A1 * | 1/2016 | Lee ........................ A61K 9/127 424/499 |

OTHER PUBLICATIONS

Maurer et al. (Urologic Oncology: Seminars and Original Investigations, 31, 2013, 1395-1401).*
Dai et al. (Cancer Biotherapy and Radiopharmaceuticals, vol. 33, No. 3, Apr. 2018, pp. 103-109).*
Gu et al. (Am J Transl Res, 2016, 8(9), 3780-3790).*
Herrmann, A. et al. (2014). "STAT3 nuclear egress requires exportin 7 via engaging lysine acetylation," *MOJ Cell Sci Report* 1(1): 9-15.

* cited by examiner

*Primary Examiner* — Amy H Bowman
(74) *Attorney, Agent, or Firm* — Mintz, Levin, Cohn, Ferris, Glovsky and Popeo, P.C.

(57) ABSTRACT

Provided herein are, inter alia, nucleic acid conjugates including a non-cell penetrating ribonucleic acid compound attached at its 3' end to a phosphorothioate polymer. Attachment of the phosphorothioate polymer to the non-cell penetrating ribonucleic acid conveys stability to and allows for efficient intracellular delivery of the non-cell penetrating ribonucleic acid. The nucleic acid conjugates provided herein including embodiments thereof are useful, inter alia, for the treatment of cancer, inflammatory disease, and pain.

16 Claims, 12 Drawing Sheets

Specification includes a Sequence Listing.

miRNA let7a-5p    modified ssDNA

PO modified miRNA let7a-5p  5'-UGAGGUAGUAGGUUGUAUAGUU-3'---LINKER---TCCATGAGCTTCCTGATGCT PS modified miRNA let7a-5p  5'-UGAGGUAGUAGGUUGUAUAGUU-3'---LINKER---T*C*C*A*T*G*A*G*C*T*T*C*C*T*G*A*T*G*C*T miR17-3p
PO modified miR17-3p   5'- ACUGCAGUGAAGGCACUUGUAG-3'---LINKER---TCCATGAGCTTCCTGATGCT
PS modified miR17-3p   5'- ACUGCAGUGAAGGCACUUGUAG-3'---LINKER---T*C*C*A*T*G*A*G*C*T*T*C*C*T*G*A*T*G*C*T modified ssDNA miRNA miR17-5p

5'-CAAAGUGCUUACAGUGCAGGUAG-3'

PO modified miR17-5p
5'-CAAAGUGCUUACAGUGCAGGUAG-3'--LINKER--TCCATGAGCTTCCTGATGCT PS modified miR17-5p
5'-CAAAGUGCUUACAGUGCAGGUAG-3'--LINKER--T*C*C*A*T*G*A*G*C*T*T*C*C*T*G*A*T*G*C*T modified ssDNA BLANK ctrl. 0.09 | miR17-5p - PO 36.3 | miR17-5p - PS 77.0

SSC-H

FL1-A :: FITC

FIG. 9 miR218-5p    modified ssDNA

PO modified miR218-5p    5'- UUGUGCUUGAUCUAACCAUGU-3'---LINKER---TCCATGAGCTTCCTGATGCT
PS modified miR218-5p    5'- UUGUGCUUGAUCUAACCAUGU-3'---LINKER---T*C*C*A*T*G*A*G*C*T*T*C*C*T*G*A*T*G*C*T

FIG. 10A

BLANK ctrl.    0.03
miR218-5p - PO    21.0
miR218-5p - PS    33.4

SSC-H

FL1-A :: FITC let7a-5p      modified sugarphosphate backbone

5'- UGAGGUAGUAGGUUGUAUAGUU -3'

PO-polymer modified let7a-5p    5'- UGAGGUAGUAGGUUGUAUAGUU -3'--LINKER--DDDDDDDDDDDDDDDDDDDD PS-polymer modified let7a-5p    5'- UGAGGUAGUAGGUUGUAUAGUU -3'--LINKER--D*D*D*D*D*D*D*D*D*D*D*D*D*D*D*D*D*D*D*D Abasic D-spacer

PHOSPHOROTHIOATE-CONJUGATED MIRNAS AND METHODS OF USING THE SAME

CROSS-REFERENCES TO RELATED APPLICATIONS

This application claims priority to U.S. Provisional Application No. 62/679,596, filed Jun. 1, 2018, which is hereby incorporated by reference in its entirety and for all purposes.

STATEMENT AS TO RIGHTS TO INVENTIONS MADE UNDER FEDERALLY SPONSORED RESEARCH AND DEVELOPMENT

This invention was made using support under Grant Number CA122976 awarded by the National Institutes of Health. The government has certain rights to this invention.

REFERENCE TO A "SEQUENCE LISTING," A TABLE, OR A COMPUTER PROGRAM LISTING APPENDIX SUBMITTED AS AN ASCII FILE

The Sequence Listing written in file 048440-685001US-_SL_ST25, created on Jun. 3, 2019, 8,799 bytes, machine format IBM-PC, MS Windows operating system, is hereby incorporated by reference.

BACKGROUND OF THE INVENTION

The manipulation of intracellular molecules involved in disease pathology is an attractive treatment option for numerous diseases. The ability to modify the activity of intracellular molecules can have profound effects on intracellular signaling pathways and result in changes in gene expression that promote favorable disease outcome. However, targeting intracellular molecules for therapeutic purposes is particularly challenging due to the need for the targeting molecule to both penetrate the cell membrane and maintain biostability in a physiological environment. Thus, there is a need in the art for biostable, cell-penetrating compositions capable of targeting intracellular molecules involved in disease pathology. Provided herein are, inter alia, compositions and methods addressing these and other needs in the art.

BRIEF SUMMARY OF THE INVENTION

In an aspect is provided a nucleic acid conjugate including: (i) a non-cell penetrating ribonucleic acid compound including the sequence of SEQ ID NO:1, SEQ ID NO:2, SEQ ID NO:3, SEQ ID NO:4 or SEQ ID NO:5; (ii) a phosphorothioate polymer; and (iii) a chemical linker attaching the phosphorothioate polymer to the 3' end of the non-cell penetrating ribonucleic acid compound; wherein the phosphorothioate polymer enhances intracellular delivery of the non-cell penetrating nucleic acid compound.

In an aspect is provided a nucleic acid conjugate including: (i) a non-cell penetrating ribonucleic acid compound including the sequence of SEQ ID NO:1; (ii) a phosphorothioate polymer; and (iii) a chemical linker attaching the phosphorothioate polymer to the 3' end of the non-cell penetrating ribonucleic acid compound; wherein the phosphorothioate polymer enhances intracellular delivery of the non-cell penetrating nucleic acid compound.

In an aspect is provided a nucleic acid conjugate including: (i) a non-cell penetrating ribonucleic acid compound including the sequence of SEQ ID NO:2; (ii) a phosphorothioate polymer; and (iii) a chemical linker attaching the phosphorothioate polymer to the 3' end of the non-cell penetrating ribonucleic acid compound; wherein the phosphorothioate polymer enhances intracellular delivery of the non-cell penetrating nucleic acid compound.

In an aspect is provided a nucleic acid conjugate including: (i) a non-cell penetrating ribonucleic acid compound including the sequence of SEQ ID NO:3; (ii) a phosphorothioate polymer; and (iii) a chemical linker attaching the phosphorothioate polymer to the 3' end of the non-cell penetrating ribonucleic acid compound; wherein the phosphorothioate polymer enhances intracellular delivery of the non-cell penetrating nucleic acid compound.

In an aspect is provided a nucleic acid conjugate including: (i) a non-cell penetrating ribonucleic acid compound including the sequence of SEQ ID NO:4; (ii) a phosphorothioate polymer; and (iii) a chemical linker attaching the phosphorothioate polymer to the 3' end of the non-cell penetrating ribonucleic acid compound; wherein the phosphorothioate polymer enhances intracellular delivery of the non-cell penetrating nucleic acid compound.

In an aspect is provided a nucleic acid conjugate including: (i) a non-cell penetrating ribonucleic acid compound including the sequence of SEQ ID NO:5; (ii) a phosphorothioate polymer; and (iii) a chemical linker attaching the phosphorothioate polymer to the 3' end of the non-cell penetrating ribonucleic acid compound; wherein the phosphorothioate polymer enhances intracellular delivery of the non-cell penetrating nucleic acid compound.

In an aspect is provided a cell including the nucleic acid conjugate provided herein including embodiments thereof.

In an aspect is provided a pharmaceutical composition including the nucleic acid conjugate as provided herein including embodiments thereof and a pharmaceutically acceptable carrier.

In an aspect is provided a method of treating cancer in a subject in need thereof. The method includes administering to the subject a therapeutically effective amount of a cell penetrating nucleic acid conjugate as provided herein including embodiments thereof, thereby treating the cancer in the subject.

In an aspect is provided a method of increasing expression of p53 in a cancer cell, the method including contacting a cancer cell with an effective amount of a cell penetrating nucleic acid conjugate as provided herein including embodiments thereof, thereby increasing expression of p53 in the cancer cell.

In an aspect is provided a method of inhibiting tumor vascularization in a subject in need thereof, the method including administering to the subject a therapeutically effective amount of a cell penetrating nucleic acid conjugate as provided herein including embodiments thereof, thereby inhibiting tumor vascularization in the subject.

In an aspect is provided a method of treating an inflammatory disease in a subject in need thereof, the method including administering to the subject a therapeutically effective amount of a cell penetrating nucleic acid conjugate as provided herein including embodiments thereof, thereby treating an inflammatory disease in the subject.

In an aspect is provided a method of treating pain in a subject in need thereof, the method including administering to the subject a therapeutically effective amount of a cell penetrating nucleic acid conjugate as provided herein including embodiments thereof, thereby treating pain in the subject.

In an aspect is provided a method of inhibiting IL-6 signaling in a cell, the method including contacting a cell with an effective amount of a cell penetrating nucleic acid conjugate as provided herein including embodiments thereof, thereby inhibiting IL-6 signaling in the cell.

In an aspect is provided a method of delivering a non-cell penetrating nucleic acid into a cell, the method including contacting a cell with the cell penetrating nucleic acid conjugate as provided herein including embodiments thereof, thereby delivering the non-cell penetrating nucleic acid into the cell.

BRIEF DESCRIPTION OF THE DRAWINGS

FIG. 2A Human multiple myeloma cells MM.1S were incubated for 30 min with 10 µg/ml modified 1et7a-3p miRNA as indicated and analyzed by flow cytometry. FIG. 2B. Human multiple myeloma cells MM.1S were incubated for 48 hrs with 10 µg/ml modified let7a-3p miRNA 48 hrs and analyzed by flow cytometry; left peak is blank control, middle peak is let7a-3p-PO; right peak is let7a-3p-PS. FIG. 2C. Human multiple myeloma cells MM.1S were incubated for 48 hrs daily with 10 µg/ml modified let7a-3p miRNA as indicated and analyzed by RT-PCR to assess expression of the STAT3 target oncogenic Bcl-xL gene. PS means that the indicated let7a-3p miRNA was elongated with phosphorothioate nucleic acids while PO means that the let7a-3p miRNA was elongated with non-phosphorothioated nucleic acids. SD shown; T-test: **) P<0.01.

FIG. 4A Human multiple myeloma cells MM.1S were incubated for 30 min as indicated with 10 µg/ml modified let7a-5p miRNA analyzed by flow cytometry. FIG. 4B Human multiple myeloma cells MM.1S were incubated for 48 hrs with 10 µg/ml modified let7a-5p miRNA and analyzed by flow cytometry; left peak is blank control, middle peak is let7a-5p-PO; right peak is let7a-5p-PS. FIG. 4C. Human multiple myeloma cells MM.1S were incubated for 48 hrs daily with 10 µg/ml modified 1et7a-5p miRNA as indicated and analyzed by RT-PCR to assess expression of the STAT3 target oncogenic Bcl-xL and IL-6 genes. PS means that the indicated let7a-5p miRNA was elongated with phosphorothioate nucleic acids while PO means that the let7a-5p miRNA was elongated with non-phosphorothioated nucleic acids. SD shown; T-test: **) P<0.01.

FIG. 6A. Human multiple myeloma cells MM.1S were incubated for 30 min with 20 µg/ml modified miR17-3p miRNA as indicated and analyzed by flow cytometry. FIG. 6B. Human multiple myeloma cells MM.1S were incubated for 48 hrs with 10 µg/ml modified miR17-3p miRNA and analyzed by flow cytometry; left peak is blank control, middle peak is miR17-3p-PO, and right peak is miR17-3p-PS. FIG. 6C. Human multiple myeloma cells MM.1S were incubated for 48 hrs daily with 10 µg/ml modified miR17-3p miRNA as indicated and analyzed by RT-PCR to assess expression of the STAT3 target oncogenic IL-6 gene. PS means that the indicated miR17-3p miRNA was elongated with phosphorothioate nucleic acids while PO means that the miR17-3p miRNA was elongated with non-phosphorothioated nucleic acids. SD shown.

FIG. 8A. Human multiple myeloma cells MM.1S were incubated for 30 min with 20 µg/ml modified miR17-5p miRNA as indicated and analyzed by flow cytometry.

FIG. 8B. Human multiple myeloma cells MM.1S were incubated for 48 hrs with 10 µg/ml modified miR17-5p miRNA and analyzed by flow cytometry; left peak is blank control, middle peak is miR17-5p-PO, and right peak is miR17-5p-PS. FIG. 8C. Human multiple myeloma cells MM.1S were incubated for 48 hrs daily with 10 µg/ml modified miR17-5p miRNA as indicated and analyzed by RT-PCR to assess expression of the STAT3 target oncogenic Bcl-xL and IL-6 genes. PS means that the indicated miR17-5p miRNA was elongated with phosphorothioate nucleic acids while PO means that the miR17-5p miRNA was elongated with non-phosphorothioated nucleic acids. SD shown.

FIG. 9: Modified miR218-5p miRNA (SEQ ID NO:5). A nucleic acid conjugate comprising a stretch of non-cell penetrating miR218-5p miRNA, a phosphorothioated nucleic acid, and a chemical linker attaching the phosphorothioated nucleic acid to the miR218-5p miRNA, is shown. To enhance intracellular delivery, the miR218-5p miRNA was extended at its 3'-end by a chemical linker followed by a 20meric ssDNA stretch. It is critical that the sugar-phosphate backbone is phosphorothioated (PS; bottom sequence of FIG. 9) indicated by (*) to achieve cellular internalization; a control miRNA was used without phosphorothioation (phosphodiester, PO; top sequence of FIG. 9).

FIGS. 10A-10C: miR218-5p miRNA (SEQ ID NO:5) intracellular delivery and reduced STAT3 target gene expression. FIG. 10A. Human multiple myeloma cells MM.1S were incubated for 30 min with 20 µg/ml modified miR218-5p miRNA as indicated and analyzed by flow cytometry. FIG. 10B. Human multiple myeloma cells MM.1S were incubated for 48 hrs with 10 µg/ml modified miR218-5p miRNA and analyzed by flow cytometry; left peak is blank control, middle peak is miR218-5p-PO, and right peak is miR218-5p-PS. FIG. 10C. Human multiple myeloma cells MM.1S were incubated for 48 hrs daily with 10 µg/ml modified miR218-5p miRNA as indicated and analyzed by RT-PCR to assess expression of the STAT3 target oncogenic Bcl-xL gene. PS means that the indicated miR218-5p miRNA was elongated with phosphorothioate nucleic acids while PO means that the miR218-5p miRNA was elongated with non-phosphorothioated nucleic acids. SD shown.

FIG. 11A. A nucleic acid conjugate comprising a stretch of non-cell penetrating 1et7a-5p miRNA is shown. To enhance intracellular delivery, the 1et7a-5p miRNA was extended at its 3'-end by a chemical linker followed by a 20meric single-stranded abasic sugar-phosphate backbone polymers (referred to as "D"). It is critical that the sugar-phosphate backbone is phosphorothioated (PS; bottom sequence of FIG. 11) indicated by (*) to achieve cellular internalization; a control miRNA was used without phosphorothioation (phosphodiester, PO; top sequence of FIG. 11). FIG. 11B. Shown is the abasic sugar-phosphate module lacking a base (a nucleic acid) in comparison to basic "spacers."

FIG. 12A. Human multiple myeloma cells MM.1S were incubated for 30 min with 20 µg/ml polymer-modified 1et7a-5p miRNA as indicated and analyzed by flow cytometry. FIG. 12B. Human multiple myeloma cells MM.1S were incubated for 48 hrs daily with 10 µg/ml polymer-modified 1et7a-5p miRNA as indicated and analyzed by RT-PCR to assess expression of the STAT3 target oncogenic Bcl-xL gene. PS means that the indicated 1et7a-5p miRNA was elongated with a phosphorothioate polymer while PO means that the 1et7a-5p miRNA was elongated with a non-phosphorothioated polymer. SD shown.

DETAILED DESCRIPTION OF THE INVENTION

Definitions

Figures 1, 2A:
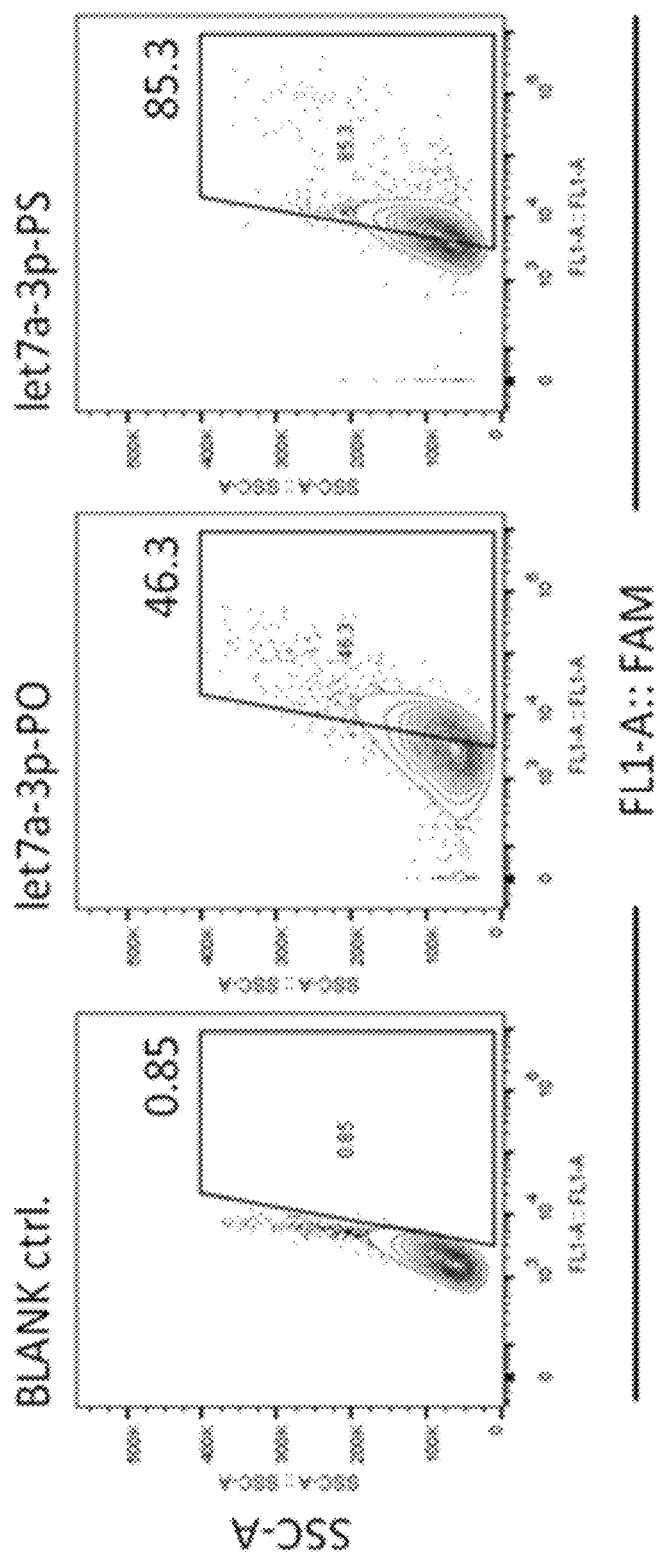
FIG. 1: Modified let7a-3p miRNA (SEQ ID NO:1). A nucleic acid conjugate including a stretch of non-cell penetrating let7a-3p miRNA, a phosphorothioated nucleic acid, and a chemical linker attaching the phosphorothioated nucleic acid to the let7a-3p miRNA, is shown. To enhance intracellular delivery, the non-cell penetrating let7a-3p miRNA sequence was extended at its 3'-end by a chemical linker followed by a 20meric ssDNA stretch. To achieve cellular internalization, it is critical that the sugar-phosphate backbone is phosphorothioated (PS; bottom sequence of FIG. 1) indicated by (*); a control miRNA was used without phosphorothioation (phosphodiester, PO; top sequence of FIG. 1).
FIGS. 2A-2C: Intracellular delivery of let7a-3p miRNA (SEQ ID NO:1) and reduced STAT3 target gene expression.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Alkyl is not cyclized. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds (e.g. alkene, alkyne). Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. Heteroalkyl is not cyclized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—

O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, —CH═CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Cycloalkyl and heterocycloalkyl are non-aromatic. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section or Drawings.

The term "oxo," as used herein, means an oxygen that is double bonded to a carbon atom.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C(O)NR"NR"'R"", —CN, —NO$_2$, monophosphate (or derivatives thereof), diphosphate (or derivatives thereof), triphosphate (or derivatives thereof), in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C(O)NR"NR"'R"", —CN, —NO$_2$, —R', —N$_3$, —CH(Ph)$_2$, fluoro($C_1$-$C_4$)alkoxy, and fluoro($C_1$-$C_4$)alkyl, monophosphate (or derivatives thereof), diphosphate (or derivatives thereof), triphosphate (or derivatives thereof), in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R"', and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R"')$_d$—, where s and d are independently integers of from 0 to 3, and X' is —O—, —S—, —S(O)—, —S(O)$_2$—, or —S(O)$_2$NR'—. The substituents R, R', R", and R"' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties: (A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), or triphosphate (or derivatives thereof), and (B) alkyl, heteroalkyl, cycloalkyl, heterocycloalkyl, aryl, heteroaryl, monophosphate (or derivatives thereof), diphosphate (or derivatives thereof), or triphosphate (or derivatives thereof), substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), or triphosphate (or derivatives thereof), and (ii) alkyl, heteroalkyl, cycloalkyl, heterocycloalkyl, aryl, heteroaryl, monophosphate (or derivatives thereof), diphosphate (or derivatives thereof), or triphosphate (or derivatives thereof), substituted with at least one substituent selected from:

(a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), or triphosphate (or derivatives thereof), and (b) alkyl, heteroalkyl, cycloalkyl, heterocycloalkyl, aryl, heteroaryl, monophosphate (or derivatives thereof), diphosphate (or derivatives thereof), or triphosphate (or derivatives thereof), substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), and triphosphate (or derivatives thereof).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The symbol "⌇" denotes the point of attachment of a chemical moiety to the remainder of a molecule or chemical formula.

A "chemical linker" or "linker" as provided herein is a covalent linker, a non-covalent linker, a peptide linker (a linker including a peptide moiety), a cleavable peptide linker, a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene or any combination thereof. Thus, a chemical linker as provided herein may include a plurality of chemical moieties, wherein each of the plurality of moieties can be chemically different.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted C$_1$-C$_{20}$ alkyl, or unsubstituted 2 to 20 membered heteroalkyl," the group may contain one or more unsubstituted C$_1$-C$_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus, a Roman alphabetic symbol may be used to distinguish each appearance of that particular R group. For example, where multiple R$^1$ substituents are present, each R$^1$ substituent may be distinguished as R$^{1A}$, R$^{1B}$, R$^{1C}$, R$^{1D}$, etc., wherein each of R$^{1A}$, R$^{1B}$, R$^{1C}$, R$^{1D}$, etc. is defined within the scope of the definition of R$^1$ and optionally differently.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a linear sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amio acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos, methyl phosphonates, chiral-methyl phosphonates, 2-O-methyl ribonucleotides, peptide-nucleic acids (PNAs) or locked nucleic acids (LNA) as known in the art), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

An "antisense nucleic acid" as referred to herein is a nucleic acid (e.g., DNA or RNA molecule) that is complementary to at least a portion of a specific target nucleic acid (e.g., STAT3) and is capable of reducing transcription of the target nucleic acid (e.g. mRNA from DNA), reducing the translation of the target nucleic acid (e.g. mRNA), altering transcript splicing (e.g. single stranded morpholino oligo), or interfering with the endogenous activity of the target nucleic acid. See, e.g., Weintraub, Scientific American, 262: 40 (1990). Typically, synthetic antisense nucleic acids (e.g. oligonucleotides) are generally between 15 and 25 bases in length. Thus, antisense nucleic acids are capable of hybridizing to (e.g. selectively hybridizing to) a target nucleic acid (e.g., STAT3). In embodiments, the antisense nucleic acid hybridizes to the target nucleic acid (e.g., STAT3) in vitro. In embodiments, the antisense nucleic acid hybridizes to the target nucleic acid (e.g., STAT3) in a cell. In embodiments, the antisense nucleic acid hybridizes to the target nucleic acid (e.g., STAT3) in an organism. In embodiments, the antisense nucleic acid hybridizes to the target nucleic acid (e.g., STAT3) under physiological conditions. Antisense nucleic acids may comprise naturally occurring nucleotides or modified nucleotides such as, e.g., phosphorothioate, methylphosphonate, and -anomeric sugar-phosphate, backbonemodified nucleotides.

In the cell, the antisense nucleic acids hybridize to the corresponding RNA (e.g., STAT3) forming a double-stranded molecule. The antisense nucleic acids interfere with the endogenous behavior of the RNA (e.g., STAT3) and inhibit its function relative to the absence of the antisense nucleic acid. Furthermore, the double-stranded molecule may be degraded via the RNAi pathway. The use of antisense methods to inhibit the in vitro translation of genes is well known in the art (Marcus-Sakura, *Anal. Biochem.*, 172:289, (1988)). Further, antisense molecules which bind directly to the DNA may be used. Antisense nucleic acids may be single or double stranded nucleic acids. Non-limiting examples of antisense nucleic acids include siRNAs (including their derivatives or pre-cursors, such as nucleotide analogs), short hairpin RNAs (shRNA), micro RNAs (miRNA), saRNAs (small activating RNAs) and small nucleolar RNAs (snoRNA) or certain of their derivatives or pre-cursors.

MicroRNAs (miRNAs) are a conserved class of small non-coding RNAs. miRNAs function as post-transcriptional regulators of gene expression, which are integral to almost all known biological processes, including cell growth, proliferation and differentiation as well as organismal metabolism and development. In the rapidly growing field of miRNAs, many miRNAs have been identified to be functionally associated with promoting either disease progression or cancer cell differentiation favoring an improved therapeutic prognosis. However, while miRNA sequences are easy to produce, a "gymnotic" administration of man-made unmodified RNA sequences fails to provide the desired therapeutic benefit.

The term "polymeric" refers to a molecule including repeating subunits (e.g., polymerized monomers). For example, polymeric molecules may be based upon polyethylene glycol (PEG), poly[amino(1-oxo-1,6-hexanediyl)], poly(oxy-1,2-ethanediyloxycarbonyl-1,4-phenylenecarbonyl), tetraethylene glycol (TEG), polyvinylpyrrolidone (PVP), poly(xylene), or poly(p-xylylene). See, for example, "Chemistry of Protein Conjugation and Cross-Linking" Shan S. Wong CRC Press, Boca Raton, Fla., USA, 1993; "BioConjugate Techniques" Greg T. Hermanson Academic Press, San Diego, Calif., USA, 1996; "Catalog of Polyethylene Glycol and Derivatives for Advanced PEGylation, 2004" Nektar Therapeutics Inc, Huntsville, Ala., USA, which are incorporated by reference in their entirety for all purposes.

The term "polymerizable monomer" is used in accordance with its meaning in the art of polymer chemistry and refers to a compound that may covalently bind chemically to other monomer molecules (such as other polymerizable monomers that are the same or different) to form a polymer.

The term "block copolymer" is used in accordance with its ordinary meaning and refers to two or more portions (e.g., blocks) of polymerized monomers linked by a covalent bond. In embodiments, a block copolymer is a repeating pattern of polymers. In embodiments, the block copolymer includes two or more monomers in a periodic (e.g., repeating pattern) sequence. For example, a diblock copolymer has the formula: -B-B-B-B-B-B-A-A-A-A-A-, where 'B' is a first subunit and 'A' is a second subunit covalently bound together. A triblock copolymer therefore is a copolymer with three distinct blocks, two of which may be the same (e.g., -A-A-A-A-A-B-B-B-B-B-A-A-A-A-A-) or all three are different (e.g., -A-A-A-A-A-B-B-B-B-B-C-C-C-C-C-) where 'A' is a first subunit, 'B' is a second subunit, and 'C' is a third subunit, covalently bound together.

The term "amphiphilic polymer" as used herein refers to a polymer containing both hydrophilic and hydrophobic portions. In embodiments, the hydrophilic to hydrophobic portions are present in a 1 to 1 mass ratio. In embodiments, the hydrophilic to hydrophobic portions are present in a 1 to 2 mass ratio. In embodiments, the hydrophilic to hydrophobic portions are present in a 1 to 5 mass ratio. In embodiments, the hydrophilic to hydrophobic portions are present in a 2 to 1 mass ratio. In embodiments, the hydrophilic to hydrophobic portions are present in a 5 to 1 mass ratio. An amphiphilic polymer may be a diblock or triblock copolymer. In embodiments, the amphiphilic polymer may include two hydrophilic portions (e.g., blocks) and one hydrophobic portion (e.g., block). In embodiments, the hydrophilic block to hydrophobic to hydrophilic ratio is 1 to 1 to 1. In embodiments, the hydrophilic block to hydrophobic to hydrophilic ratio is 1.8 to 1 to 1.8. In embodiments, the hydrophilic block to hydrophobic to hydrophilic ratio is 2 to 1 to 2. In embodiments, the hydrophilic block to hydrophobic to hydrophilic ratio is 1 to 1 to 2.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanidine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and a non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein the complementarity of sequences may be partial, in which only some of the nucleic acids match according to base pairing, or complete, where all the nucleic acids match according to base pairing. Thus, two sequences that are complementary to each other, may have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region).

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The term "phosphorothioate nucleic acid" refers to a nucleic acid in which one or more internucleotide linkages are through a phosphorothioate moiety (thiophosphate) moiety. The phosphorothioate moiety may be a monothiophosphate ($—P(O)_3(S)^{3-}—$) or a dithiophosphate ($—P(O)_2(S)_2^{3-}—$). In embodiments of all the aspects provided herein, the phosphorothioate moiety is a monothiophosphate ($—P(O)_3(S)^{3-}—$). That is, in embodiments of all the aspects provided herein, the phosphorothioate nucleic acid is a monothiophosphate nucleic acid. In embodiments, one or more of the nucleosides of a phosphorothioate nucleic acid are linked through a phosphorothioate moiety (e.g. monothiophosphate) moiety, and the remaining nucleosides are linked through a phosphodiester moiety ($—P(O)_4^{3-}—$). In embodiments, one or more of the nucleosides of a phosphorothioate nucleic acid are linked through a phosphorothioate moiety (e.g. monothiophosphate) moiety, and the remaining nucleosides are linked through a methylphosphonate linkage. In embodiments, all the nucleosides of a phosphorothioate nucleic acid are linked through a phosphorothioate moiety (e.g. a monothiophosphate) moiety.

Phosphorothioate oligonucleotides (phosphorothioate nucleic acids) are typically from about 5, 6, 7, 8, 9, 10, 12, 15, 25, 30, 40, 50 or more nucleotides in length, up to about 100 nucleotides in length. Phosphorothioate nucleic acids may also be longer in lengths, e.g., 200, 300, 500, 1000, 2000, 3000, 5000, 7000, 10,000, etc. As described above, in certain embodiments. the phosphorothioate nucleic acids herein contain one or more phosphodiester bonds. In other embodiments, the phosphorothioate nucleic acids include alternate backbones (e.g., mimics or analogs of phosphodiesters as known in the art, such as, boranophosphate, methylphosphonate, phosphoramidate, or O-methylphosphoroamidite linkages (see Eckstein, Oligonucleotides and Analogues: A Practical Approach, Oxford University Press). The phosphorothioate nucleic acids may also include one or more nucleic acid analog monomers known in the art, such as, peptide nucleic acid monomer or polymer, locked nucleic acid monomer or polymer, morpholino monomer or polymer, glycol nucleic acid monomer or polymer, or threose nucleic acid monomer or polymer. Other analog nucleic acids include those with positive backbones; non-ionic backbones, and nonribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. Phosphorothioate nucleic acids and phosphorothioate polymer backbones can be linear or branched. For example, the branched nucleic acids are repetitively branched to form higher ordered structures such as dendrimers and the like.

As used herein, a "phosphorothioate polymer backbone" is a chemical polymer with at least two phosphorothioate linkages (e.g. monothiophosphate) (e.g. linking together sugar subunits, cyclic subunits or alkyl subunits). The phosphorothioate polymer backbone may be a phosphorothioate sugar polymer (i.e., a polymer composed of abasic sugar-phosphate modules), which is a phosphorothioate nucleic acid in which one or more (or all) of the chain of pentose sugars lack the bases (nucleobases) normally present in a nucleic acid. The phosphorothioate polymer backbone can include two or more phosphorothioate linkages. The phosphorothioate polymer backbone can include 5, 6, 7, 8, 9, 10, 12, 15, 25, 30, 40, 50 or more linkages and can contain up to about 100 phosphorothioate linkages. Phosphorothioate polymer backbones may also contain a larger number of linkages, e.g., 200, 300, 500, 1000, 2000, 3000, 5000, 7000, 10,000, and the like.

The phosphorothioate nucleic acids and phophorothioate polymer backbones may be partially or completely phosphorothioated. For example, 50% or more of the interneucleotide linkages of a phosphorothioate nucleic acid can be phosphorothioate linkages. Optionally, 5%, 10%, 15%, 20%, 25%, 30%, 35%, 40%, 45%, 50%, 55%, 60%, 65%, 70%, 75%, 80%, 85%, 90%, 95%, or 99% of the internucleotide linkages of a phosphorothioate nucleic acid are phosphorothioate linkages. Optionally, 50%, 55%, 60%, 65%, 70%, 75%, 80%, 85%, 90%, 95%, or 99% of the internucleotide linkages of a phosphorothioate nucleic acid are phosphorothioate linkages. Optionally, 75%, 80%, 85%, 90%, 95%, or 99% of the internucleotide linkages of a phosphorothioate nucleic acid are phosphorothioate linkages. Optionally, 90%, 95%, or 99% of the internucleotide linkages of a phosphorothioate nucleic acid are phosphorothioate linkages. In embodiments, the remaining internucleotide linkages are phosphodiester linkages. In embodiments, the remaining internucleotide linkages are methylphosphonate linkages. Optionally, 100% of the internucleotide linkages of the phosphorothioate nucleic acids are phosphorothioate linkages. Similarly, 5%, 10%, 15%, 20%, 25%, 30%, 35%, 40%, 45%, 50%, 55%, 60%, 65%, 70%, 75%, 80%, 85%, 90%, 95%, or 99%, of the intersugar linkages in a phosphorothioate polymer backbone can be phosphorothioate linkages. Optionally, 50%, 55%, 60%, 65%, 70%, 75%, 80%, 85%, 90%, 95%, or 99%, of the intersugar linkages in a phosphorothioate polymer backbone can be phosphorothioate linkages. Optionally, 75%, 80%, 85%, 90%, 95%, or 99%, of the intersugar linkages in a phosphorothioate polymer backbone can be phosphorothioate linkages. Optionally, 90%, 95%, or 99%, of the intersugar linkages in a phosphorothioate polymer backbone can be phosphorothioate linkages. In embodiments, the remaining internucleotide linkages are phosphodiester linkages. In embodiments, the remaining internucleotide linkages are methylphosphonate linkages. Optionally, 100% of the intersugar linkages of the phosphorothioate polymer backbone are phosphorothioate linkages.

A "labeled nucleic acid or oligonucleotide" is one that is bound, either covalently, through a linker or a chemical bond, or noncovalently, through ionic, van der Waals, electrostatic, or hydrogen bonds to a label such that the presence of the nucleic acid may be detected by detecting the presence of the detectable label bound to the nucleic acid. Alternatively, a method using high affinity interactions may achieve the same results where one of a pair of binding partners binds to the other, e.g., biotin, streptavidin. In embodiments, the phosphorothioate nucleic acid or phosphorothioate polymer backbone includes a detectable label, as disclosed herein and generally known in the art. In embodiments, the phosphorothioate nucleic acid or phosphorothioate polymer backbone is connected to a detectable label through a chemical linker.

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

The phosphorothioate nucleic acids and phosphorothioate polymer backbones provided herein can include one or more reactive moieties, e.g., a covalent reactive moiety. A reactive moiety may be attached to the remainder of the phosphorothioate nucleic acids and phosphorothioate polymer backbones using any appropriate linker, such as a polymer linker known in the art or alternatively a polyethylene glygcol linker or equivalent. The linker may, in embodiments, include (i.e. be attached to) a detectable label as described herein. As used herein, the term "covalent reactive moiety" refers to a chemical moiety capable of chemically reactive with an amino acid of a non-cell penetrating protein, as described herein, to form a covalent bond and, thus, a conjugate as provided herein.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and 0-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

The terms "numbered with reference to" or "corresponding to," when used in the context of the numbering of a given amino acid or polynucleotide sequence, refer to the numbering of the residues of a specified reference sequence when the given amino acid or polynucleotide sequence is compared to the reference sequence. An amino acid residue in a protein "corresponds" to a given residue when it occupies the same essential structural position within the protein as the given residue. One skilled in the art will immediately recognize the identity and location of residues corresponding to a specific position in a protein (e.g., STAT3) in other proteins with different numbering systems. For example, by performing a simple sequence alignment with a protein (e.g., STAT3) the identity and location of residues corresponding to specific positions of said protein are identified in other protein sequences aligning to said protein. For example, a selected residue in a selected protein corresponds to lysine at position 685 when the selected residue occupies the same essential spatial or other structural relationship as a lysine at position 685. In some embodiments, where a selected protein is aligned for maximum homology with a protein, the position in the aligned selected protein aligning with lysine 685 is said to correspond to lysine 685. Instead of a primary sequence alignment, a three dimensional structural alignment can also be used, e.g., where the structure of the selected protein is aligned for maximum correspondence with the lysine at position 685, and the overall structures compared. In this case, an amino acid that occupies the same essential position as lysine 685 in the structural model is said to correspond to the lysine 685 residue.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

The terms "STAT3," "STAT3 protein," "STAT3 peptide" as referred to herein include any of the recombinant or naturally-occurring forms of the Signal transducer and activator of transcription 3 (STAT3) protein or variants or homologs thereof that maintain STAT3 protein activity (e.g. within at least 50%, 80%, 90%, 95%, 96%, 97%, 98%, 99% or 100% activity compared to STAT3). In some aspects, the variants or homologs have at least 90%, 95%, 96%, 97%, 98%, 99% or 100% amino acid sequence identity across the whole sequence or a portion of the sequence (e.g. a 10, 20, 50, 100, 150 or 200 continuous amino acid portion) compared to a naturally occurring STAT3 polypeptide. In embodiments, the STAT3 peptide is substantially identical to the protein identified by the UniProt reference number P40763 or a variant or homolog having substantial identity thereto. In embodiments, the STAT3 peptide includes the sequence of SEQ ID NO:8. In embodiments, the STAT3 peptide is the sequence of SEQ ID NO:8.

The term "IL-6" or "Interleukin 6" as referred to herein includes any of the recombinant or naturally-occurring forms of the IL-6 protein or variants or homologs thereof that maintain IL-6 protein activity (e.g. within at least 50%, 80%, 90%, 95%, 96%, 97%, 98%, 99% or 100% activity compared to IL-6). IL-6 is a member of the interleukin family and acts as both a pro-inflammatory cytokine and an anti-inflammatory myokine. In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IL-6 polypeptide. In embodiments, the IL-6 protein is substantially identical to the protein identified by the UniProt reference number P05231 or a variant or homolog having substantial identity thereto.

As used herein, the terms "cell-penetrating" or "cell-penetration" refer to the ability of a molecule (e.g. a protein) to pass from the extracellular environment into a cell in a significant or effective amount. Thus, a cell-penetrating conjugate is a molecule that passes from the extracellular environment, through the membrane, and into a cell.

As used herein, the terms "non-cell penetrating" or "non-cell penetration" refers to the inability of a molecule to pass from the extracellular environment into a cell in a significant or effective amount. Thus, non-cell penetrating nucleic acids or ribonucleic acid compounds generally are not capable of passing from the extracellular environment, through the cell membrane, and into a cell in order to achieve a significant biological effect on a population of cells, organ or organism. The term does not exclude the possibility that one or more of the small number of nucleic acids or ribonucleic acid compounds may enter the cell. However, the term refers to molecules that are generally not able to enter a cell from the extracellular environment to a significant degree. Examples of non-cell penetrating molecules and substances include, but are not limited to, large molecules such as, for example, high molecular weight proteins, nucleic acids or ribonucleic acid compounds. Nucleic acids or ribonucleic acid compounds can be determined to be non-cell penetrating using methods known to those of skill in the art. By way of example, a nucleic acid or ribonucleic acid compound can be fluorescently labeled and the ability of the nucleic acid or ribonucleic acid compound to pass from the extracellular environment into the cell can be determined in vitro by flow cytometric analysis or confocal microscopy. In some embodiments, a "non-cell penetrating nucleic acid or ribonucleic acid compound" refers to a nucleic acid or ribonucleic acid compound that penetrates a cell at least about 2, 3, 4, 5, 6, 7, 8, 9, 10, 20, 30, 40, 50, 60, 70, 80, 90, 100, 200, 300, 400, 500, 600, 700, 800, 900, 1000, 10,000 or 100,000 fold less than the same nucleic acid or ribonucleic acid compound attached to a phosphorothioate nucleic acid or phosphorothioate polymer backbone. In some embodiments, a "non-cell penetrating nucleic acid or ribonucleic acid compound" refers to a nucleic acid or ribonucleic acid compound that does not measurably penetrate a cell.

As used herein, the term "intracellular" means inside a cell. As used herein, an "intracellular target" is a target, e.g., nucleic acid, polypeptide or other molecule (e.g., carbohydrate) that is located inside of a cell and is a target to which the non-cell penetrating nucleic acids or ribonucleic acid compounds provided herein bind. Binding can be direct or indirect. Optionally, the non-cell penetrating nucleic acid or ribonucleic acid compound selectively binds the intracellular target. By selectively binds, selectively binding, or specifically binding refers to the agent (e.g., a non-cell penetrating nucleic acid or ribonucleic acid compound) binding one agent (e.g., intracellular target) to the partial or complete exclusion of other agents. By binding is meant a detectable binding at least about 1.5 times the background of the assay method. For selective or specific binding such a detectable binding can be detected for a given agent but not a control agent. Alternatively, or additionally, the detection of binding can be determined by assaying the presence of down-stream molecules or events.

As used herein, the term "conjugate" refers to the association between atoms or molecules. The association can be direct or indirect. For example, a conjugate between a nucleic acid and a protein or nucleic acid or ribonucleic acid compound can be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). Optionally, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the phosphorothioate nucleic acid and phosphorothioate backbone polymer are non-covalently attached to the nucleic acid or ribonucleic acid compound through a non-covalent chemical reaction between a component of the phosphorothioate nucleic acid and phosphorothioate backbone polymer (e.g., a monothiophosphate) and a component of the nucleic acid or ribonucleic acid compound.

A "cell" as used herein, refers to a cell carrying out metabolic or other functions sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

The term "activating," as used herein, refers to an nucleic acid conjugate capable of detectably increasing the expression or activity of a given gene or protein (e.g., p53). The activating nucleic acid conjugate can increase expression or activity 10%, 20%, 30%, 40%, 50%, 60%, 70%, 80%, 90% or more in comparison to a control in the absence of the activating nucleic acid. In certain instances, expression or activity is 1.5-fold, 2-fold, 3-fold, 4-fold, 5-fold, 10-fold or higher than the expression or activity in the absence of the activating nucleic acid conjugate.

As defined herein, the term "inhibition", "inhibit", "inhibiting" and the like in reference to an nucleic acid conjugate interaction means negatively affecting (e.g. decreasing) the activity or function of a protein (e.g., STAT3) relative to the activity or function of the protein in the absence of the inhibitor. In embodiments inhibition refers to reduction of a disease or symptoms of disease. Thus, in embodiments, inhibition includes, at least in part, partially or totally blocking stimulation, decreasing, preventing, or delaying activation, or inactivating, desensitizing, or down-regulating signal transduction or enzymatic activity or the amount of a protein.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a non-cell penetrating nucleic acid compound (e.g., 1et7a-3p (SEQ ID NO:1), 1et7a-5p (SEQ ID NO:2), miR17-3p (SEQ ID NO:3), miR17-5p (SEQ ID NO:4), miR218-5p (SEQ ID NO:5)) as described herein and an intracellular target (e.g., STAT3 (SEQ ID NO:8)).

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "control" or "standard control" refers to a sample, measurement, or value that serves as a reference, usually a known reference, for comparison to a test sample, measurement, or value. For example, a test sample can be taken from a patient suspected of having a given disease (e.g. an autoimmune disease, inflammatory autoimmune disease, cancer, infectious disease, immune disease, or other disease) and compared to a known normal (non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. A standard control value can also be obtained from the same individual, e.g. from an earlier-obtained sample from the patient prior to disease onset. One of skill will recognize that standard controls can be designed for assessment of any number of parameters (e.g. RNA levels, protein levels, specific cell types, specific bodily fluids, specific tissues, synoviocytes, synovial fluid, synovial tissue, fibroblast-like synoviocytes, macrophage-like synoviocytes, etc).

One of skill in the art will understand which standard controls are most appropriate in a given situation and be able to analyze data based on comparisons to standard control values.

Standard controls are also valuable for determining the significance (e.g. statistical significance) of data. For example, if values for a given parameter are widely variant in standard controls, variation in test samples will not be considered as significant.

The terms "subject," "patient," "individual," etc. are not intended to be limiting and can be generally interchanged. That is, an individual described as a "patient" does not necessarily have a given disease, but may be merely seeking medical advice.

The terms "disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma). The disease may be an autoimmune, inflammatory, cancer, infectious, metabolic, developmental, cardiovascular, liver, intestinal, endocrine, neurological, or other disease.

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma (cutaneous T-cell lymphoma), sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, oat cell carcinoma, carcinoma ossificans, osteoid carcinoma, papillary carcinoma, periportal carcinoma, pre-invasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tubular carcinoma, tuberous carcinoma, verrucous carcinoma, or carcinoma *villosum*.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

As used herein, "treating" or "treatment of" a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean prolonging survival of a subject beyond that expected in the absence of treatment. "Treating" can also mean inhibiting the progression of the condition, disorder or disease, slowing the progression of the condition, disorder or disease temporarily, although in some instances, it involves halting the progression of the condition, disorder or disease permanently. As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

The terms "dose" and "dosage" are used interchangeably herein. A dose refers to the amount of active ingredient given to an individual at each administration. The dose will vary depending on a number of factors, including the range of normal doses for a given therapy, frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical or pharmaceutical composition, and depends on the route of administration. For example, a dosage form can be in a liquid form for nebulization, e.g., for inhalants, in a tablet or liquid, e.g., for oral delivery, or a saline solution, e.g., for injection.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "therapeutically effective dose or amount" as used herein is meant a dose that produces effects for which it is administered (e.g. treating or preventing a disease). The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)). For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a standard control. A therapeutically effective dose or amount may ameliorate one or more symptoms of a disease. A therapeutically effective dose or amount may prevent or delay the onset of a disease or one or more symptoms of a disease when the effect for which it is being administered is to treat a person who is at risk of developing the disease.

As used herein, the term "pharmaceutically acceptable" is used synonymously with "physiologically acceptable" and "pharmacologically acceptable". A pharmaceutical composition will generally comprise agents for buffering and preservation in storage, and can include buffers and carriers for appropriate delivery, depending on the route of administration.

Nucleic Acid Conjugates

Provided herein are, inter alia, nucleic acid conjugates including a non-cell penetrating ribonucleic acid compound attached at its 3' end to a phosphorothioate polymer. The ribonucleic acid compounds conjugated to phophorothioate polymers at their 3' end exhibit suprising biostability and can be delivered intracellulary with high efficiency. Upon entry into a cell the non-cell penetrating ribonucleic acid compounds provided herein may target and modify the activity of intracellular molecules involved in disease pathology thereby improving disease outcome. The nucleic acid conjugates provided herein including embodiments thereof are useful, inter alia, for the treatment of cancer, inflammatory disease, and pain.

In an aspect is provided a nucleic acid conjugate including: (i) a non-cell penetrating ribonucleic acid compound including the sequence of SEQ ID NO:1, SEQ ID NO:2, SEQ ID NO:3, SEQ ID NO:4 or SEQ ID NO:5; (ii) a phosphorothioate polymer; and (iii) a chemical linker attaching the phosphorothioate polymer to the 3' end of the non-cell penetrating ribonucleic acid compound; wherein the phosphorothioate polymer enhances intracellular delivery of the non-cell penetrating nucleic acid compound.

In embodiments, the non-cell penetrating ribonucleic acid compound includes the sequence of SEQ ID NO:1. In embodiments, the non-cell penetrating ribonucleic acid compound includes the sequence of SEQ ID NO:2. In embodiments, the non-cell penetrating ribonucleic acid compound includes the sequence of SEQ ID NO:3. In embodiments, the non-cell penetrating ribonucleic acid compound includes the sequence of SEQ ID NO:4. In embodiments, the non-cell penetrating ribonucleic acid compound includes the sequence of SEQ ID NO:5.

In embodiments, the non-cell penetrating ribonucleic acid compound is the sequence of SEQ ID NO:1. In embodiments, the non-cell penetrating ribonucleic acid compound is the sequence of SEQ ID NO:2. In embodiments, the non-cell penetrating ribonucleic acid compound is the sequence of SEQ ID NO:3. In embodiments, the non-cell penetrating ribonucleic acid compound is the sequence of SEQ ID NO:4. In embodiments, the non-cell penetrating ribonucleic acid compound is the sequence of SEQ ID NO:5.

In embodiments, the non-cell penetrating ribonucleic acid compound is a micro RNA (miRNA).

In embodiments, the non-cell penetrating ribonucleic acid compound is about 10, 20, 30, 40, 50, 60, 70, 80, 90 or more residues in length. In embodiments, the non-cell penetrating ribonucleic acid compound is more than about 10 residues in length. In embodiments, the non-cell penetrating ribonucleic acid compound is more than about 20 residues in length. In embodiments, the non-cell penetrating ribonucleic acid compound is more than about 30 residues in length. In embodiments, the non-cell penetrating ribonucleic acid compound is more than about 40 residues in length. In embodiments, the non-cell penetrating ribonucleic acid compound is more than about 50 residues in length. In embodiments, the non-cell penetrating ribonucleic acid compound is more than about 60 residues in length. In embodiments, the non-cell penetrating ribonucleic acid compound is more than about 70 residues in length. In embodiments, the non-cell penetrating ribonucleic acid compound is more than about 80 residues in length. In embodiments, the non-cell penetrating ribonucleic acid compound is more than about 90 residues in length.

In embodiments, the non-cell penetrating ribonucleic acid compound is about 10 residues in length. In embodiments, the non-cell penetrating ribonucleic acid compound is 10 residues in length. In embodiments, the non-cell penetrating ribonucleic acid compound is about 20 residues in length. In embodiments, the non-cell penetrating ribonucleic acid compound is 20 residues in length.

In embodiments, the non-cell penetrating ribonucleic acid compound is about 21 residues in length. In embodiments, the non-cell penetrating ribonucleic acid compound is 21 residues in length. In embodiments, the non-cell penetrating ribonucleic acid compound is about 22 residues in length. In embodiments, the non-cell penetrating ribonucleic acid compound is 22 residues in length. In embodiments, the non-cell penetrating ribonucleic acid compound is about 23 residues in length. In embodiments, the non-cell penetrating ribonucleic acid compound is 23 residues in length. In embodiments, the non-cell penetrating ribonucleic acid compound is about 24 residues in length. In embodiments, the non-cell penetrating ribonucleic acid compound is 24 residues in length. In embodiments, the non-cell penetrating ribonucleic acid compound is about 25 residues in length. In embodiments, the non-cell penetrating ribonucleic acid compound is 25 residues in length. In embodiments, the non-cell penetrating ribonucleic acid compound is about 26 residues in length.

In embodiments, the non-cell penetrating ribonucleic acid compound is 26 residues in length. In embodiments, the non-cell penetrating ribonucleic acid compound is about 27 residues in length. In embodiments, the non-cell penetrating ribonucleic acid compound is 27 residues in length. In embodiments, the non-cell penetrating ribonucleic acid compound is about 28 residues in length. In embodiments, the non-cell penetrating ribonucleic acid compound is 28 residues in length. In embodiments, the non-cell penetrating ribonucleic acid compound is about 29 residues in length. In embodiments, the non-cell penetrating ribonucleic acid compound is 29 residues in length. In embodiments, the non-cell penetrating ribonucleic acid compound is about 30 residues in length. In embodiments, the non-cell penetrating ribonucleic acid compound is 30 residues in length.

In embodiments, the non-cell penetrating ribonucleic acid compound is about 40 residues in length. In embodiments, the non-cell penetrating ribonucleic acid compound is 40 residues in length. In embodiments, the non-cell penetrating ribonucleic acid compound is about 50 residues in length. In embodiments, the non-cell penetrating ribonucleic acid compound is 50 residues in length. In embodiments, the non-cell penetrating ribonucleic acid compound is about 60 residues in length. In embodiments, the non-cell penetrating ribonucleic acid compound is 60 residues in length. In embodiments, the non-cell penetrating ribonucleic acid compound is about 70 residues in length. In embodiments, the non-cell penetrating ribonucleic acid compound is 70 residues in length. In embodiments, the non-cell penetrating ribonucleic acid compound is about 80 residues in length. In embodiments, the non-cell penetrating ribonucleic acid compound is 80 residues in length. In embodiments, the non-cell penetrating ribonucleic acid compound is about 90 residues in length. In embodiments, the non-cell penetrating ribonucleic acid compound is 90 residues in length.

In embodiments, the non-cell penetrating ribonucleic acid compound is from about 20 to about 30 residues in length. In embodiments, the non-cell penetrating ribonucleic acid compound is from 20 to 30 residues in length. In embodiments, the non-cell penetrating ribonucleic acid compound is from about 21 to about 30 residues in length. In embodiments, the non-cell penetrating ribonucleic acid compound is from 21 to 30 residues in length. In embodiments, the non-cell penetrating ribonucleic acid compound is from about 22 to about 30 residues in length. In embodiments, the non-cell penetrating ribonucleic acid compound is from 22 to 30 in length. In embodiments, the non-cell penetrating ribonucleic acid compound is from about 23 to about 30 residues in length. In embodiments, the non-cell penetrating ribonucleic acid compound is from 23 to 30 residues in length. In embodiments, the non-cell penetrating ribonucleic acid compound is from about 24 to about 30 residues in length. In embodiments, the non-cell penetrating ribonucleic acid compound is from 24 to 30 residues in length.

In embodiments, the non-cell penetrating ribonucleic acid compound is from about 25 to about 30 residues in length. In embodiments, the non-cell penetrating ribonucleic acid compound is from 25 to 30 residues in length. In embodiments, the non-cell penetrating ribonucleic acid compound is from about 26 to about 30 residues in length. In embodiments, the non-cell penetrating ribonucleic acid compound is from 26 to 30 residues in length. In embodiments, the non-cell penetrating ribonucleic acid compound is from about 27 to about 30 residues in length. In embodiments, the non-cell penetrating ribonucleic acid compound is from 27 to 30 residues in length. In embodiments, the non-cell penetrating ribonucleic acid compound is from about 28 to about 30 residues in length. In embodiments, the non-cell penetrating ribonucleic acid compound is from 28 to 30 residues in length.

In embodiments, the non-cell penetrating ribonucleic acid compound is from about 20 to about 29 residues in length. In embodiments, the non-cell penetrating ribonucleic acid compound is from 20 to 29 residues in length. In embodiments, the non-cell penetrating ribonucleic acid compound is from about 20 to about 28 residues in length. In embodiments, the non-cell penetrating ribonucleic acid compound is from 20 to 28 residues in length. In embodiments, the non-cell penetrating ribonucleic acid compound is from about 20 to about 27 residues in length. In embodiments, the non-cell penetrating ribonucleic acid compound is from 20 to 27 residues in length. In embodiments, the non-cell penetrating ribonucleic acid compound is from about 20 to about 26 residues in length. In embodiments, the non-cell penetrating ribonucleic acid compound is from 20 to 26 residues in length.

In embodiments, the non-cell penetrating ribonucleic acid compound is from about 20 to about 25 residues in length. In embodiments, the non-cell penetrating ribonucleic acid compound is from 20 to 25 residues in length. In embodiments, the non-cell penetrating ribonucleic acid compound is from about 20 to about 24 residues in length. In embodiments, the non-cell penetrating ribonucleic acid compound is from 20 to 24 residues in length. In embodiments, the non-cell penetrating ribonucleic acid compound is from about 20 to about 23 residues in length. In embodiments, the non-cell penetrating ribonucleic acid compound is from 20 to 23 residues in length. In embodiments, the non-cell penetrating ribonucleic acid compound is from about 20 to about 22 residues in length. In embodiments, the non-cell penetrating ribonucleic acid compound is from 20 to 22 residues in length.

In embodiments, the non-cell penetrating ribonucleic acid compound is from about 21 to about 25 residues in length. In embodiments, the non-cell penetrating ribonucleic acid compound is from 21 to 25 residues in length. In embodiments, the non-cell penetrating ribonucleic acid compound is from about 22 to about 25 residues in length. In embodiments, the non-cell penetrating ribonucleic acid compound is from 22 to 25 residues in length. In embodiments, the non-cell penetrating ribonucleic acid compound is from about 23 to about 25 residues in length. In embodiments, the non-cell penetrating ribonucleic acid compound is from 23 to 25 residues in length.

In embodiments, the phosphorothioate polymer is a phosphorothioate nucleic acid or an abasic sugar-phosphorothioated polymer. An "abasic sugar-phosphate polymer" as provided herein refers to a polymer including abasic sugar moieties (i.e. a moiety including a ribose or deoxyribose aromatic ring that does not have a base attached to it, which is not substituted with a base), wherein the abasic sugar moieties are covalently linked to other abasic sugar moieties or to sugar moieties substituted with a base and wherein the moieties are connected through a phosphodiester bond or a phosphorothioate bond. In embodiments, the phosphorothioate polymer is a phosphorothioate nucleic acid. In embodiments, the phosphorothioate polymer is an abasic sugar-phosphorothioated polymer. In embodiments, the phosphorothioate polymer is a phosphorothioate deoxyribonucleic acid.

In embodiments, the phosphorothioate polymer is about 10, 20, 30, 40, 50, 60, 70, 80, 90, 100 or more residues in length. In embodiments, the phosphorothioate polymer is about 10 residues in length. In embodiments, the phosphorothioate polymer is 10 residues in length. In embodiments, the phosphorothioate polymer is more than about 10 residues in length. In embodiments, the phosphorothioate polymer is more than 10 residues in length. In embodiments, the phosphorothioate polymer is about 20 residues in length. In embodiments, the phosphorothioate polymer is 20 residues in length. In embodiments, the phosphorothioate polymer is more than about 20 residues in length. In embodiments, the phosphorothioate polymer is more than 20 residues in length. In embodiments, the phosphorothioate polymer is about 30 residues in length. In embodiments, the phosphorothioate polymer is 30 residues in length. In embodiments, the phosphorothioate polymer is more than about 30 residues in length. In embodiments, the phosphorothioate polymer is more than 30 residues in length.

In embodiments, the phosphorothioate polymer is about 40 residues in length. In embodiments, the phosphorothioate polymer is 40 residues in length. In embodiments, the phosphorothioate polymer is more than about 40 residues in length. In embodiments, the phosphorothioate polymer is more than 40 residues in length. In embodiments, the phosphorothioate polymer is about 50 residues in length. In embodiments, the phosphorothioate polymer is 50 residues in length. In embodiments, the phosphorothioate polymer is more than about 50 residues in length. In embodiments, the phosphorothioate polymer is more than 50 residues in length. In embodiments, the phosphorothioate polymer is about 60 residues in length. In embodiments, the phosphorothioate polymer is 60 residues in length. In embodiments, the phosphorothioate polymer is more than about 60 residues in length. In embodiments, the phosphorothioate polymer is more than 60 residues in length.

In embodiments, the phosphorothioate polymer is about 70 residues in length. In embodiments, the phosphorothioate polymer is 70 residues in length. In embodiments, the phosphorothioate polymer is more than about 70 residues in length. In embodiments, the phosphorothioate polymer is more than 70 residues in length. In embodiments, the phosphorothioate polymer is about 80 residues in length. In embodiments, the phosphorothioate polymer is 80 residues in length. In embodiments, the phosphorothioate polymer is more than about 80 residues in length. In embodiments, the phosphorothioate polymer is more than 80 residues in length. In embodiments, the phosphorothioate polymer is about 90 residues in length. In embodiments, the phosphorothioate polymer is 90 residues in length. In embodiments, the phosphorothioate polymer is more than about 90 residues in length. In embodiments, the phosphorothioate polymer is more than 90 residues in length. In embodiments, the phosphorothioate polymer is about 100 residues in length. In embodiments, the phosphorothioate polymer is 100 residues in length.

In embodiments, the phosphorothioate polymer is from about 10 to about 30 residues in length. In embodiments, the phosphorothioate polymer is from 10 to 30 residues in length. In embodiments, the phosphorothioate polymer is from about 11 to about 30 residues in length. In embodiments, the phosphorothioate polymer is from 11 to 30 residues in length. In embodiments, the phosphorothioate polymer is from about 12 to about 30 residues in length. In embodiments, the phosphorothioate polymer is from 12 to 30 in length. In embodiments, the phosphorothioate polymer is from about 13 to about 30 residues in length. In embodiments, the phosphorothioate polymer is from 13 to 30 residues in length. In embodiments, the phosphorothioate polymer is from about 14 to about 30 residues in length. In embodiments, the phosphorothioate polymer is from 14 to 30 residues in length.

In embodiments, the phosphorothioate polymer is from about 15 to about 30 residues in length. In embodiments, the phosphorothioate polymer is from 15 to 30 residues in length. In embodiments, the phosphorothioate polymer is from about 16 to about 30 residues in length. In embodiments, the phosphorothioate polymer is from 16 to 30 residues in length. In embodiments, the phosphorothioate polymer is from about 17 to about 30 residues in length. In embodiments, the phosphorothioate polymer is from 17 to 30 residues in length. In embodiments, the phosphorothioate polymer is from about 18 to about 30 residues in length. In embodiments, the phosphorothioate polymer is from 18 to 30 residues in length. In embodiments, the phosphorothioate polymer is from about 19 to about 30 residues in length. In embodiments, the phosphorothioate polymer is from 19 to 30 residues in length.

In embodiments, the phosphorothioate polymer is from about 20 to about 30 residues in length. In embodiments, the phosphorothioate polymer is from 20 to 30 residues in length. In embodiments, the phosphorothioate polymer is from about 21 to about 30 residues in length. In embodiments, the phosphorothioate polymer is from 21 to 30 residues in length. In embodiments, the phosphorothioate polymer is from about 22 to about 30 residues in length. In embodiments, the phosphorothioate polymer is from 22 to 30 in length. In embodiments, the phosphorothioate polymer is from about 23 to about 30 residues in length. In embodiments, the phosphorothioate polymer is from 23 to 30 residues in length. In embodiments, the phosphorothioate polymer is from about 24 to about 30 residues in length. In embodiments, the phosphorothioate polymer is from 24 to 30 residues in length.

In embodiments, the phosphorothioate polymer is from about 25 to about 30 residues in length. In embodiments, the phosphorothioate polymer is from 25 to 30 residues in length. In embodiments, the phosphorothioate polymer is from about 26 to about 30 residues in length. In embodiments, the phosphorothioate polymer is from 26 to 30 residues in length. In embodiments, the phosphorothioate polymer is from about 27 to about 30 residues in length. In embodiments, the phosphorothioate polymer is from 27 to 30 residues in length. In embodiments, the phosphorothioate polymer is from about 28 to about 30 residues in length. In embodiments, the phosphorothioate polymer is from 28 to 30 residues in length.

In embodiments, the phosphorothioate polymer is from about 10 to about 29 residues in length. In embodiments, the phosphorothioate polymer is from 10 to 29 residues in length. In embodiments, the phosphorothioate polymer is from about 10 to about 28 residues in length. In embodiments, the phosphorothioate polymer is from 10 to 28 residues in length. In embodiments, the phosphorothioate polymer is from about 10 to about 27 residues in length. In embodiments, the phosphorothioate polymer is from 10 to 27 residues in length. In embodiments, the phosphorothioate polymer is from about 10 to about 26 residues in length. In embodiments, the phosphorothioate polymer is from 10 to 26 residues in length. In embodiments, the phosphorothioate polymer is from about 10 to about 25 residues in length. In embodiments, the phosphorothioate polymer is from 10 to 25 residues in length.

In embodiments, the phosphorothioate polymer is from about 10 to about 24 residues in length. In embodiments, the phosphorothioate polymer is from 10 to 24 residues in length. In embodiments, the phosphorothioate polymer is from about 10 to about 23 residues in length. In embodiments, the phosphorothioate polymer is from 10 to 23 residues in length. In embodiments, the phosphorothioate polymer is from about 10 to about 22 residues in length. In embodiments, the phosphorothioate polymer is from 10 to 22 residues in length. In embodiments, the phosphorothioate polymer is from about 10 to about 21 residues in length. In embodiments, the phosphorothioate polymer is from 10 to 21 residues in length.

In embodiments, the phosphorothioate polymer is from about 10 to about 20 residues in length. In embodiments, the phosphorothioate polymer is from 10 to 20 residues in length. In embodiments, the phosphorothioate polymer is from about 10 to about 19 residues in length. In embodiments, the phosphorothioate polymer is from 10 to 19 residues in length. In embodiments, the phosphorothioate polymer is from about 10 to about 18 residues in length. In embodiments, the phosphorothioate polymer is from 10 to 18 residues in length. In embodiments, the phosphorothioate polymer is from about 10 to about 17 residues in length. In embodiments, the phosphorothioate polymer is from 10 to 17 residues in length. In embodiments, the phosphorothioate polymer is from about 10 to about 16 residues in length. In embodiments, the phosphorothioate polymer is from 10 to 16 residues in length.

In embodiments, the phosphorothioate polymer is from about 10 to about 15 residues in length. In embodiments, the phosphorothioate polymer is from 10 to 15 residues in length. In embodiments, the phosphorothioate polymer is from about 10 to about 14 residues in length. In embodiments, the phosphorothioate polymer is from 10 to 14 residues in length. In embodiments, the phosphorothioate polymer is from about 10 to about 13 residues in length. In embodiments, the phosphorothioate polymer is from 10 to 13 residues in length. In embodiments, the phosphorothioate polymer is from about 10 to about 12 residues in length. In embodiments, the phosphorothioate polymer is from 10 to 12 residues in length.

In embodiments, the phosphorothioate polymer is about 20 residues in length. In embodiments, the phosphorothioate polymer is 20 residues in length.

In embodiments, the phosphorothioate polymer includes the sequence of SEQ ID NO:6 or SEQ ID NO:7. In embodiments, the phosphorothioate polymer includes the sequence of SEQ ID NO:6. In embodiments, the phosphorothioate polymer is SEQ ID NO:6. In embodiments, the phosphorothioate polymer includes the sequence of SEQ ID NO:7 In embodiments, the phosphorothioate polymer is SEQ ID NO:7.

In embodiments, the phosphorothioate polymer is single-stranded. In embodiments, the phosphorothioate nucleic acid is a single-stranded phosphorothioate nucleic acid. In embodiments, the abasic sugar-phosphorothioated polymer is a single-stranded abasic sugar-phosphorothioated polymer.

The conjugates provided herein including embodiments thereof may include a ribonucleic acid compound attached to a phosphorothioate polymer through a chemical linker. In embodiments, the chemical linker is a covalent linker.

In embodiments, the chemical linker is a covalent linker. In embodiments, the linker includes the structure of formula:

(I)

In formula (I), $R^1$ is hydrogen, halogen, —$CF_3$, —CN, —$CCl_3$, —COOH, —$CH_2$COOH, —$CONH_2$, —OH, —SH, —$NO_2$, —$NH_2$, —$NHNH_2$, —$ONH_2$, —NHC=(O)$NHNH_2$, substituted (e.g., substituted with substituent group(s), size-limited substituent group(s), or lower substituent group(s)) or unsubstituted alkyl, substituted (e.g., substituted with substituent group(s), size-limited substituent group(s), or lower substituent group(s)) or unsubstituted heteroalkyl, substituted (e.g., substituted with substituent group(s), size-limited substituent group(s), or lower substituent group(s)) or unsubstituted cycloalkyl, substituted (e.g., substituted with substituent group(s), size-limited substituent group(s), or lower substituent group(s)) or unsubstituted heterocycloalkyl, substituted (e.g., substituted with substituent group(s), size-limited substituent group(s), or lower substituent group(s)) or unsubstituted aryl, or substituted (e.g., substituted with substituent group(s), size-limited substituent group(s), or lower substituent group(s)) or unsubstituted heteroaryl.

In embodiments, $R^1$ is hydrogen, halogen, —$CF_3$, —CN, —$CCl_3$, —COOH, —$CH_2$COOH, —$CONH_2$, —OH, —SH, —$NO_2$, —$NH_2$, —$NHNH_2$, —$ONH_2$, —NHC=(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl.

In embodiments, the linker is -$L^1$-$L^2$-$L^3$-$L^4$-$L^5$-$L^6$-$L^7$-. In embodiments, $L^1$ is a bond, —NH—N=CH—, —S(O)$_2$—, —$NR^2$—, —O—, —S—, —C(O)—, —C(O)NH—, —NHC(O)—, —NHC(O)NH—, —C(O)O—, —OC(O)—, substituted (e.g., substituted with substituent group(s), size-limited substituent group(s), or lower substituent group(s)) or unsubstituted alkylene, substituted (e.g., substituted with substituent group(s), size-limited substituent group(s), or lower substituent group(s)) or unsubstituted heteroalkylene, substituted (e.g., substituted with substituent group(s), size-limited substituent group(s), or lower substituent group(s)) or unsubstituted cycloalkylene, substituted (e.g., substituted with substituent group(s), size-limited substituent group(s), or lower substituent group(s)) or unsubstituted heterocycloalkylene, substituted (e.g., substituted with substituent group(s), size-limited substituent group(s), or lower substituent group(s)) or unsubstituted arylene, or substituted (e.g., substituted with substituent group(s), size-limited substituent group(s), or lower substituent group(s)) or unsubstituted heteroarylene.

In embodiments, $L^2$ is a bond, —NH—N=CH—, —S(O)$_2$—, —NR$^2$—, —O—, —S—, —C(O)—, —C(O)NH—, —NHC(O)—, —NHC(O)NH—, —C(O)O—, —OC(O)—, substituted (e.g., substituted with substituent group(s), size-limited substituent group(s), or lower substituent group(s)) or unsubstituted alkylene, substituted (e.g., substituted with substituent group(s), size-limited substituent group(s), or lower substituent group(s)) or unsubstituted heteroalkylene, substituted (e.g., substituted with substituent group(s), size-limited substituent group(s), or lower substituent group(s)) or unsubstituted cycloalkylene, substituted (e.g., substituted with substituent group(s), size-limited substituent group(s), or lower substituent group(s)) or unsubstituted heterocycloalkylene, substituted (e.g., substituted with substituent group(s), size-limited substituent group(s), or lower substituent group(s)) or unsubstituted arylene, or substituted (e.g., substituted with substituent group(s), size-limited substituent group(s), or lower substituent group(s)) or unsubstituted heteroarylene.

In embodiments, $L^3$ is a bond, —NH—N=CH—, —S(O)$_2$—, —NR$^2$—, —O—, —S—, —C(O)—, —C(O)NH—, —NHC(O)—, —NHC(O)NH—, —C(O)O—, —OC(O)—, substituted (e.g., substituted with substituent group(s), size-limited substituent group(s), or lower substituent group(s)) or unsubstituted alkylene, substituted (e.g., substituted with substituent group(s), size-limited substituent group(s), or lower substituent group(s)) or unsubstituted heteroalkylene, substituted (e.g., substituted with substituent group(s), size-limited substituent group(s), or lower substituent group(s)) or unsubstituted cycloalkylene, substituted (e.g., substituted with substituent group(s), size-limited substituent group(s), or lower substituent group(s)) or unsubstituted heterocycloalkylene, substituted (e.g., substituted with substituent group(s), size-limited substituent group(s), or lower substituent group(s)) or unsubstituted arylene, or substituted (e.g., substituted with substituent group(s), size-limited substituent group(s), or lower substituent group(s)) or unsubstituted heteroarylene.

In embodiments, $L^4$ is a bond, —NH—N=CH—, —S(O)$_2$—, —NR$^2$—, —O—, —S—, —C(O)—, —C(O)NH—, —NHC(O)—, —NHC(O)NH—, —C(O)O—, —OC(O)—, substituted (e.g., substituted with substituent group(s), size-limited substituent group(s), or lower substituent group(s)) or unsubstituted alkylene, substituted (e.g., substituted with substituent group(s), size-limited substituent group(s), or lower substituent group(s)) or unsubstituted heteroalkylene, substituted (e.g., substituted with substituent group(s), size-limited substituent group(s), or lower substituent group(s)) or unsubstituted cycloalkylene, substituted (e.g., substituted with substituent group(s), size-limited substituent group(s), or lower substituent group(s)) or unsubstituted heterocycloalkylene, substituted (e.g., substituted with substituent group(s), size-limited substituent group(s), or lower substituent group(s)) or unsubstituted arylene, or substituted (e.g., substituted with substituent group(s), size-limited substituent group(s), or lower substituent group(s)) or unsubstituted heteroarylene.

In embodiments, $L^5$ is a bond, —NH—N=CH—, —S(O)$_2$—, —NR$^2$—, —O—, —S—, —C(O)—, —C(O)NH—, —NHC(O)—, —NHC(O)NH—, —C(O)O—, —OC(O)—, substituted (e.g., substituted with substituent group(s), size-limited substituent group(s), or lower substituent group(s)) or unsubstituted alkylene, substituted (e.g., substituted with substituent group(s), size-limited substituent group(s), or lower substituent group(s)) or unsubstituted heteroalkylene, substituted (e.g., substituted with substituent group(s), size-limited substituent group(s), or lower substituent group(s)) or unsubstituted cycloalkylene, substituted (e.g., substituted with substituent group(s), size-limited substituent group(s), or lower substituent group(s)) or unsubstituted heterocycloalkylene, substituted (e.g., substituted with substituent group(s), size-limited substituent group(s), or lower substituent group(s)) or unsubstituted arylene, or substituted (e.g., substituted with substituent group(s), size-limited substituent group(s), or lower substituent group(s)) or unsubstituted heteroarylene.

In embodiments, $L^6$ is a bond, —NH—N=CH—, —S(O)$_2$—, —NR$^2$—, —O—, —S—, —C(O)—, —C(O)NH—, —NHC(O)—, —NHC(O)NH—, —C(O)O—, —OC(O)—, substituted (e.g., substituted with substituent group(s), size-limited substituent group(s), or lower substituent group(s)) or unsubstituted alkylene, substituted (e.g., substituted with substituent group(s), size-limited substituent group(s), or lower substituent group(s)) or unsubstituted heteroalkylene, substituted (e.g., substituted with substituent group(s), size-limited substituent group(s), or lower substituent group(s)) or unsubstituted cycloalkylene, substituted (e.g., substituted with substituent group(s), size-limited substituent group(s), or lower substituent group(s)) or unsubstituted heterocycloalkylene, substituted (e.g., substituted with substituent group(s), size-limited substituent group(s), or lower substituent group(s)) or unsubstituted arylene, or substituted (e.g., substituted with substituent group(s), size-limited substituent group(s), or lower substituent group(s)) or unsubstituted heteroarylene.

In embodiments, $L^7$ is a bond, —NH—N=CH—, —S(O)$_2$—, —NR$^2$—, —O—, —S—, —C(O)—, —C(O)NH—, —NHC(O)—, —NHC(O)NH—, —C(O)O—, —OC(O)—, substituted (e.g., substituted with substituent group(s), size-limited substituent group(s), or lower substituent group(s)) or unsubstituted alkylene, substituted (e.g., substituted with substituent group(s), size-limited substituent group(s), or lower substituent group(s)) or unsubstituted heteroalkylene, substituted (e.g., substituted with substituent group(s), size-limited substituent group(s), or lower substituent group(s)) or unsubstituted cycloalkylene, substituted (e.g., substituted with substituent group(s), size-limited substituent group(s), or lower substituent group(s)) or unsubstituted heterocycloalkylene, substituted (e.g., substituted with substituent group(s), size-limited substituent group(s), or lower substituent group(s)) or unsubstituted arylene, or substituted (e.g., substituted with substituent group(s), size-limited substituent group(s), or lower substituent group(s)) or unsubstituted heteroarylene.

In embodiments, the linker is a non-immunogenic linker.

In embodiments, the conjugate includes a detectable moiety. In embodiments, the detectable moiety is attached to the non-cell penetrating ribonucleic acid compound. In embodiments, the detectable moiety is attached to the phosphorothioate polymer. In embodiments, the detectable moiety forms part of the linker. In embodiments, the detectable moiety is covalently attached to the linker.

The non-cell penetrating ribonucleic acid compounds provided herein including embodiments thereof are useful for the treatment of cancer, inflammatory disease, and/or pain by modifying the activity of intracellular molecules. In embodiments, the conjugate as provided herein including embodiments thereof is bound to an intracellular target. Thus, in embodiments, the non-cell penetrating ribonucleic acid compound inhibits the activity or expression of an intracellular target. In embodiments, the non-cell penetrating ribonucleic acid compound inhibits the activity of an intracellular target. In embodiments, the non-cell penetrating ribonucleic acid compound inhibits the expression of an intracellular target. In embodiments, the intracellular target is a signaling molecule or transcription factor. In embodiments, the intracellular target is a signaling molecule. In embodiments, the intracellular target is a transcription factor. In embodiments, the signaling molecule is a phosphatase or kinase. In embodiments, the signaling molecule is a phosphatase. In embodiments, the signaling molecule is a kinase.

In embodiments, the intracellular target is a transcription factor. In embodiments, the intracellular target is STAT3. In embodiments, the intracellular target is a STAT3 protein including the amino acid sequence of SEQ ID NO:8. In embodiments, the intracellular target is the amino acid sequence of SEQ ID NO:8. [

In embodiments, the non-cell penetrating ribonucleic acid compound includes a ribonucleic acid compound which inhibits STAT3 activity relative to a standard control. In embodiments, the non-cell penetrating ribonucleic acid compound is a ribonucleic acid compound which inhibits STAT3 activity relative to a standard control. In embodiments, the non-cell penetrating ribonucleic acid compound includes a ribonucleic acid compound, which inhibits expression of a STAT3 target gene relative to a standard control. In embodiments, the non-cell penetrating ribonucleic acid compound is a ribonucleic acid compound, which inhibits expression of a STAT3 target gene relative to a standard control. In embodiments, the STAT3 target gene is an oncogene. In embodiments, the STAT3 target gene comprises Bcl-xL or IL-6. In embodiments, the STAT3 target gene comprises Bcl-xL. In embodiments, the STAT3 target gene comprises IL-6. In embodiments, the STAT3 target gene is Bcl-xL or IL-6. In embodiments, the STAT3 target gene is Bcl-xL. In embodiments, the STAT3 target gene is IL-6.

In an aspect is provided a cell including a nucleic acid conjugate as described herein including embodiments thereof. In embodiments, the cell is a breast cancer cell, a prostate cancer cell, an ovarian cancer cell, a brain cancer cell, a pancreatic cancer cell, a melanoma cell, a colon cancer cell, a gastric cancer cell, a head-and-neck cancer cell, a liver cancer cell, a lung cancer cell, a cervical cancer cell, a sarcoma cell, a leukemia cell, a lymphoma cell, a multiple myeloma cell or a metastatic lung cancer cell. In embodiments, the cell is a breast cancer cell. In embodiments, the cell is a prostate cancer cell. In embodiments, the cell is an ovarian cancer cell. In embodiments, the cell is a brain cancer cell. In embodiments, the cell is a pancreatic cancer cell. In embodiments, the cell is a melanoma cell. In embodiments, the cell is a colon cancer cell. In embodiments, the cell is a gastric cancer cell. In embodiments, the cell is a head-and-neck cancer cell. In embodiments, the cell is a liver cancer cell. In embodiments, the cell is a lung cancer cell. In embodiments, the cell is a cervical cancer cell. In embodiments, the cell is a sarcoma cell. In embodiments, the cell is a leukemia cell. In embodiments, the cell is a lymphoma cell. In embodiments, the cell is a multiple myeloma cell. In embodiments, the cell is a metastatic lung cancer cell.

Pharmaceutical Compositions

The conjugates provided herein including embodiments thereof are further contemplated as forming part of a pharmaceutical composition. Therefore, in an aspect is provided a pharmaceutical composition including the nucleic acid conjugate as described herein including embodiments thereof and a pharmaceutically acceptable carrier.

Pharmaceutical compositions provided by the present invention include compositions wherein the active ingredient (e.g. compositions described herein, including embodiments thereof) is contained in a therapeutically effective amount, i.e., in an amount effective to achieve its intended purpose. The actual amount effective for a particular application will depend, inter alia, on the condition being treated. When administered in methods to treat a disease, the conjugates described herein will contain an amount of active ingredient effective to achieve the desired result, e.g., modulating the activity of a target molecule, and/or reducing, eliminating, or slowing the progression of disease symptoms. Determination of a therapeutically effective amount of a conjugate of the invention is within the capabilities of those skilled in the art.

The compositions for administration will commonly include an agent as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In some embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the active compounds or constructs in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The formulations of compounds can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer and severity of such symptoms), kind of concurrent treatment, complications from the disease being treated or other health-related problems. Other therapeutic regimens or agents can be used in conjunction with the methods and compounds of the invention. Adjustment and manipulation of established dosages (e.g., frequency and duration) are well within the ability of those skilled in the art.

For any composition (e.g., the conjugates provided herein including embodiments thereof) described herein, the therapeutically effective amount can be initially determined from cell culture assays. Target concentrations will be those concentrations of active compound(s) that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred "Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Methods of Treating Cancer

The conjugates as provided herein including embodiments thereof are useful, inter alia, for the treatment of cancer. Thus, in an aspect, a method for treating cancer in a subject in need thereof is provided. The method includes administering to the subject a therapeutically effective amount of a cell penetrating nucleic acid conjugate as described herein including embodiments thereof, thereby treating the cancer in the subject.

In embodiments, the cancer is breast cancer, prostate cancer, ovarian cancer, brain cancer, pancreatic cancer, melanoma, colon cancer, gastric cancer, head-and-neck cancer, liver cancer, lung cancer, cervical cancer, sarcoma, leukemia, lymphoma, multiple myeloma. In embodiments, the cancer is breast cancer. In embodiments, the cancer is prostate cancer. In embodiments, the cancer is ovarian cancer. In embodiments, the cancer is brain cancer. In embodiments, the cancer is pancreatic cancer. In embodiments, the cancer is melanoma. In embodiments, the cancer is colon cancer. In embodiments, the cancer is gastric cancer. In embodiments, the cancer is head-and-neck cancer. In embodiments, the cancer is liver cancer. In embodiments, the cancer is lung cancer. In embodiments, the cancer is cervical cancer. In embodiments, the cancer is sarcoma. In embodiments, the cancer is leukemia. In embodiments, the cancer is lymphoma. In embodiments, the cancer is multiple myeloma. In embodiments, the cancer is metastatic lung cancer.

In embodiments, the method includes decreasing in the subject an expression level of BIRC5 or BclXL relative to a standard control. In embodiments, the method includes decreasing in the subject an expression level of BIRC5 and BclXL relative to a standard control. In embodiments, the method includes decreasing in the subject an expression level of BIRC5 relative to a standard control. In embodiments, the method includes decreasing in the subject an expression level of BclXL relative to a standard control. In embodiments, the standard control is an expression level of BIRC5 or BclXL detected in the absence of a cell penetrating nucleic acid conjugate as described herein including embodiments thereof.

The term "BIRC5," also known as "survivin", as referred to herein includes any of the recombinant or naturally-occurring forms of the gene encoding baculoviral inhibitor of apoptosis repeat-containing 5 (BIRC5), homologs or variants thereof that maintain BIRC5 activity (e.g. within at least 50%, 80%, 90%, 95%, 96%, 97%, 98%, 99% or 100% activity compared to BIRC5). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring BIRC5 polypeptide. In embodiments, the BIRC5 gene is substantially identical to the nucleic acid identified by the ENSEMBLE reference number ENSG00000089685 or a variant having substantial identity thereto. The expression level of BRIC5 may be determined by detecting levels of BIRC5 mRNA or protein using methods known in the art. In embodiments, the BIRC5 mRNA is the nucleic acid sequence as identified by the Ensembl ID: ENST00000301633.8, homolog or functional fragment thereof. In embodiments, the BIRC5 protein is the amino acid sequence as identified by Uniprot reference number O15392, homolog or functional fragment thereof.

The term "Bcl-xL," also known as BCL2L1, as referred to herein includes any of the recombinant or naturally-occurring forms of the gene encoding B-cell lymphoma-extra large (BclXL), homologs or variants thereof that maintain Bcl-xL activity (e.g. within at least 50%, 80%, 90%, 95%, 96%, 97%, 98%, 99% or 100% activity compared to Bcl-xL). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Bcl-XL polypeptide. In embodiments, the BclXL gene is substantially identical to the nucleic acid identified by the ENSEMBLE reference number ENSG00000171552 or a variant having substantial identity thereto. The expression level of BclXL may be determined by detecting levels of BclXL mRNA or protein using methods known in the art.

In embodiments, the BclXL mRNA is the nucleic acid sequence as identified by the Ensembl ID: ENST00000307677.4, homolog or functional fragment thereof. In embodiments, the BIRC5 protein is the amino acid sequence as identified by Uniprot reference number Q07817, homolog or functional fragment thereof.

Methods of Increasing P53 In a Cell

The conjugates provided herein including embodiments thereof are further contemplated as a means of increasing p53 in a cell. A "p53 protein" or "p53" as referred to herein includes any of the recombinant or naturally-occurring forms of the tumor protein p53 (p53) or variants or homologs thereof that maintain p53 activity (e.g. within at least 50%, 80%, 90%, 95%, 96%, 97%, 98%, 99% or 100% activity compared top53). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring p53 protein. In embodiments, the p53 protein is substantially identical to the protein identified by the UniProt reference number P04637 or a variant or homolog having substantial identity thereto.

In an aspect, a method of increasing expression of p53 in a cancer cell is provided, the method including contacting a cancer cell with an effective amount of a cell penetrating nucleic acid conjugate as described herein including embodiments thereof, thereby increasing expression of p53 in the cancer cell.

Methods of Inhibiting Tumor Vascularization

The conjugates provided herein including embodiments thereof are useful for the treatment of cancer through inhibition of tumor vascularization. Thus, in another aspect, a method of inhibiting tumor vascularization in a subject in need thereof is provided, the method including administering to the subject a therapeutically effective amount of a cell penetrating nucleic acid conjugate as described herein including embodiments thereof, thereby inhibiting tumor vascularization in the subject.

Methods of Treating an Inflammatory Disease

The conjugates provided herein including embodiments thereof are also useful for the treatment of inflammatory disease. Therefore, in another aspect, a method of treating an inflammatory disease in a subject in need thereof is provided, the method including administering to the subject a therapeutically effective amount of a cell penetrating nucleic acid conjugate as described herein including embodiments thereof, thereby treating an inflammatory disease in the subject.

As used herein, the term "inflammatory disease" refers to a disease or condition characterized by aberrant inflammation (e.g., an increased level of inflammation compared to a control such as a healthy person not suffering from a disease). Examples of inflammatory diseases include traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis.

In embodiments, the method includes decreasing in the subject an expression level of FGA, IL1B or SERPINA3 relative to a standard control. In embodiments, the method includes decreasing in the subject an expression level of FGA, IL1B and SERPINA3 relative to a standard control. In embodiments, the method includes decreasing in the subject an expression level of FGA relative to a standard control. In embodiments, the method includes decreasing in the subject an expression level of IL1B relative to a standard control. In embodiments, the method includes decreasing in the subject an expression level of SERPINA3 relative to a standard control. In embodiments, the standard control is an expression level of FGA, IL1B or SERPINA3 detected in the absence of a cell penetrating nucleic acid conjugate as described herein including embodiments thereof.

The term "FGA" as referred to herein includes any of the recombinant or naturally-occurring forms of the gene encoding fibrinogen alpha chain (FGA), homologs or variants thereof that maintain FGA activity (e.g. within at least 50%, 80%, 90%, 95%, 96%, 97%, 98%, 99% or 100% activity compared to FGA). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring FGA polypeptide. In embodiments, the FGA gene is substantially identical to the nucleic acid identified by the ENSEMBLE reference number ENSG00000171560 or a variant having substantial identity thereto. The expression level of FGA may be determined by detecting levels of FGA mRNA or protein using methods known in the art. In embodiments, the FGA mRNA is the nucleic acid sequence as identified by the Ensembl ID: ENST00000302053.7, homolog or functional fragment thereof. In embodiments, the FGA protein is the amino acid sequence as identified by Uniprot reference number P02671, homolog or functional fragment thereof.

The term "IL1B" as referred to herein includes any of the recombinant or naturally-occurring forms of the gene encoding interleukin 1 beta (IL1B), homologs or variants thereof that maintain IL1B activity (e.g. within at least 50%, 80%, 90%, 95%, 96%, 97%, 98%, 99% or 100% activity compared to IL1B). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring IL1B polypeptide. In embodiments, the IL1B gene is substantially identical to the nucleic acid identified by the ENSEMBLE reference number ENSG00000125538 or a variant having substantial identity thereto. The expression level of IL1B may be determined by detecting levels of IL1B mRNA or protein using methods known in the art. In embodiments, the IL1B mRNA is the nucleic acid sequence as identified by the Ensembl ID: ENST00000263341.6, homolog or functional fragment thereof. In embodiments, the IL1B protein is the amino acid sequence as identified by Uniprot reference number P01584, homolog or functional fragment thereof.

The term "SERPINA3" as referred to herein includes any of the recombinant or naturally-occurring forms of the gene encoding alpha 1-antichymotrypsin, homologs or variants thereof that maintain alpha 1-antichymotrypsin activity (e.g. within at least 50%, 80%, 90%, 95%, 96%, 97%, 98%, 99% or 100% activity compared to alpha 1-antichymotrypsin). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring alpha 1-antichymotrypsin polypeptide. In embodiments, the SERPINA3 gene is substantially identical to the nucleic acid identified by the ENSEMBLE reference number ENSG00000196136 or a variant having substantial identity thereto. The expression level of SERPINA3 may be determined by detecting levels of SERPINA3 mRNA or protein using methods known in the art. In embodiments, the SERPINA mRNA is the nucleic acid sequence as identified by the Ensembl ID: ENST00000467132.5, homolog or functional fragment thereof. In embodiments, the alpha 1-antichymotrypsin protein is the amino acid sequence as identified by Uniprot reference number P01011, homolog or functional fragment thereof.

Non-Opioid-Based Methods of Treating Pain

Opioids are a class of compound among the most widely used for treatment of pain. Opioid drugs produce effects by interacting with opioid receptors. Opioids have opium- or morphine-like properties allowing them to act as opioid receptor agonists. However, opioids have other pharmacological effects including drowsiness, respiratory depression, and constipation, as well as abuse potential and tolerance. The negative side-effects of opioid use have spurred a need for non-opioid-based pain treatments. Provided herein are, inter alia, non-opioid-based methods for treating pain in a subject in need thereof.

In an aspect, a method of treating pain in a subject in need thereof is provided. The method includes administering to the subject a therapeutically effective amount of a cell penetrating nucleic acid conjugate as described herein including embodiments thereof, thereby treating pain in the subject.

The pain may emanate from a wide variety of sources or be derived from a wide variety of causes. Thus, the pain may be nociceptive pain (e.g., trauma, procedural, cut, sprains, bone fractures, burns, bumps, bruises), neuropathic pain (e.g., post herpetic neuralgia, reflex sympathetic dystrophy/causalgia, cancer pain, pain induced by treatment of cancer, HIV/AIDS or hepatitis, diabetes, phantom limb pain, entrapment neuropathy, chronic alcohol use, exposure to other toxins, vitamin deficiencies and idiopathic), inflammatory pain (e.g., arthritis, colitis, carditis, pulmonits, nephritis, myositis, vasculitis, endometriosis, neuritis, dermatitis and pain associated with other inflammatory conditions), chronic widespread pain (e.g., fibromyalgia, migraine, irritable bowel syndrome, syndrome X, interstitial bladder syndrome, chronic fatigue syndrome, post-traumatic stress disorder, pain associated with psychiatric illnesses such as anxiety and depression and stress-related pain conditions, and secondary to inflammatory or neuropathic pain syndromes) or mixed etiology (i.e., combinations of two or more of the above four categories).

In embodiments, the nucleic acid conjugates useful for treating pain in the methods provided herein does not mediate its analgesic effect through opioid receptors. In embodiments, the nucleic acid conjugate useful for treating pain in the methods provided herein does not have opium- or morphine-like properties. In embodiments, the nucleic acid conjugate useful for treating pain in the methods provided herein is not an opioid receptor ligand. In embodiments, the nucleic acid conjugate useful for treating pain in the methods provided herein does not bind to an opioid receptor. In embodiments, the nucleic acid conjugate useful for treating pain in the methods provided herein is not an opioid receptor agonist.

In embodiments, the method includes decreasing in the subject an expression level of PTGS1, PTGS2, CALCA or SST relative to a standard control. In embodiments, the method includes decreasing in the subject an expression level of PTGS1, PTGS2, CALCA and SST relative to a standard control. In embodiments, the method includes decreasing in the subject an expression level of PTG51 relative to a standard control. In embodiments, the method includes decreasing in the subject an expression level of PTG52 relative to a standard control. In embodiments, the method includes decreasing in the subject an expression level of CALCA relative to a standard control. In embodiments, the method includes decreasing in the subject an expression level of SST relative to a standard control. In embodiments, the standard control is an expression level of PTGS1, PTGS2, CALCA or SST detected in the absence of a cell penetrating nucleic acid conjugate as described herein including embodiments thereof.

The term "PTGS1" as referred to herein includes any of the recombinant or naturally-occurring forms of the gene encoding prostaglandin-endoperoxide synthase 1 (PTGS1), also known as COX-1, homologs or variants thereof that maintain PTGS1 activity (e.g. within at least 50%, 80%, 90%, 95%, 96%, 97%, 98%, 99% or 100% activity compared to PTGS1). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PTGS1 polypeptide. In embodiments, the PTGS1 gene is substantially identical to the nucleic acid identified by the ENSEMBLE reference number ENSG00000095303 or a variant having substantial identity thereto. The expression level of PTGS1 may be determined by detecting levels of PTGS1 mRNA or protein using methods known in the art. In embodiments, the PTGS1 mRNA is the nucleic acid sequence as identified by the Ensembl ID: ENST00000540753.5, homolog or functional fragment thereof. In embodiments, the PTGS1 protein is the amino acid sequence as identified by Uniprot reference number P23219, homolog or functional fragment thereof.

The term "PTGS2" as referred to herein includes any of the recombinant or naturally-occurring forms of the gene encoding prostaglandin-endoperoxide synthase 2 (PTGS2), also known as COX-2, homologs or variants thereof that maintain PTGS2 activity (e.g. within at least 50%, 80%, 90%, 95%, 96%, 97%, 98%, 99% or 100% activity compared to PTGS2). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PTGS2 polypeptide. In embodiments, the PTGS2 gene is substantially identical to the nucleic acid identified by the ENSEMBLE reference number ENSG00000073756 or a variant having substantial identity thereto. The expression level of PTGS2 may be determined by detecting levels of PTGS2 mRNA or protein using methods known in the art. In embodiments, the PTGS2 mRNA is the nucleic acid sequence as identified by the Ensembl ID: ENST00000367468.9, homolog or functional fragment thereof. In embodiments, the PTGS2 protein is the amino acid sequence as identified by Uniprot reference number P35354, homolog or functional fragment thereof.

The term "SST" as referred to herein includes any of the recombinant or naturally-occurring forms of the gene encoding somatostatin (SST), homologs or variants thereof that maintain SST activity (e.g. within at least 50%, 80%, 90%, 95%, 96%, 97%, 98%, 99% or 100% activity compared to SST). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring SST polypeptide. In embodiments, the SST gene is substantially identical to the nucleic acid identified by the ENSEMBLE reference number ENSG00000157005 or a variant having substantial identity thereto. The expression level of SST may be determined by detecting levels of SST mRNA or protein using methods known in the art. In embodiments, the SST mRNA is the nucleic acid sequence as identified by the Ensembl ID: ENST00000287641.3, homolog or functional fragment thereof. In embodiments, the SST protein is the amino acid sequence as identified by Uniprot reference number P61278, homolog or functional fragment thereof.

The term "CALCA" as referred to herein includes any of the recombinant or naturally-occurring forms of the gene encoding calcitonin gene-related peptide (CGRP), homologs or variants thereof that maintain CALCA activity (e.g. within at least 50%, 80%, 90%, 95%, 96%, 97%, 98%, 99% or 100% activity compared to CALCA). In some aspects, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CALCA polypeptide. In embodiments, the CALCA gene is substantially identical to the nucleic acid identified by the ENSEMBLE reference number ENSG00000110680 or a variant having substantial identity thereto. The expression level of CALCA may be determined by detecting levels of CALCA mRNA or protein using methods known in the art. In embodiments, the CALCA mRNA is the nucleic acid sequence as identified by the Ensembl ID: ENST00000361010.7, homolog or functional fragment thereof. In embodiments, the CALCA protein is the amino acid sequence as identified by Uniprot reference numbers P01258, P06881, homolog or functional fragment thereof.

Methods of Decreasing Il-6 Signaling in a Cell

The conjugates provided herein including embodiments thereof are useful for decreasing IL-6 signaling in a cell. Thus, in an aspect, a method of inhibiting IL-6 signaling in a cell is provided, the method including contacting a cell with an effective amount of a cell penetrating nucleic acid conjugate as provided herein including embodiments thereof, thereby inhibiting IL-6 signaling in the cell.

Methods of Delivering a Non-Cell Penetrating Nucleic Acid into a Cell

The conjugates provided herein including embodiments thereof are useful for delivering non-cell penetrating nucleic acids into a cell. In an aspect is provided a method of delivering a non-cell penetrating nucleic acid into a cell, the method including contacting a cell with the cell penetrating nucleic acid conjugate as provided herein including embodiments thereof, thereby delivering the non-cell penetrating nucleic acid into the cell.

EXAMPLES

Here, Applicants describe a gymnotic administration of miRNAs, for example, 1et7a-3p (SEQ ID NO:1), 1et7a-5p (SEQ ID NO:2), miR17-3p (SEQ ID NO:3), miR17-5p (SEQ ID NO:4), miR218-5p (SEQ ID NO:5), by protecting the operating miRNA sequences through extending the miRNAs on their 3' ends with phosphorothioated ssDNA oligonucleotides or phosphorothioated single-stranded abasic sugar-phosphate backbone polymers. Applicants show that attachment of phosphorothioated ssDNA oligonucleotides or phosphorothioated single-stranded abasic sugar-phosphate backbone polymers to miRNAs on the 3' ends of the miRNAs facilitates intracellular delivery of miRNAs into tumor cells and subsequent target of their target genes as well as protection of miRNAs from enzymatic degradation in serum.

Example 1: Production of Cell Internalizing Nucleic Acid Compounds Via Covalent Linkage to Phosphorothioated SSDNA Oligonucelotides miRNAs with naturally occurring sequences were fused covalently to phosphorothioated ssDNA (PS) 20meric oligo to facilitate cellular internalization targeting intracellular molecular targets. A non-phosphorothioated, phosphodiester ssDNA oligo (P0) extension of the miRNAs was employed as a non-internalizing control.

Figure 3:
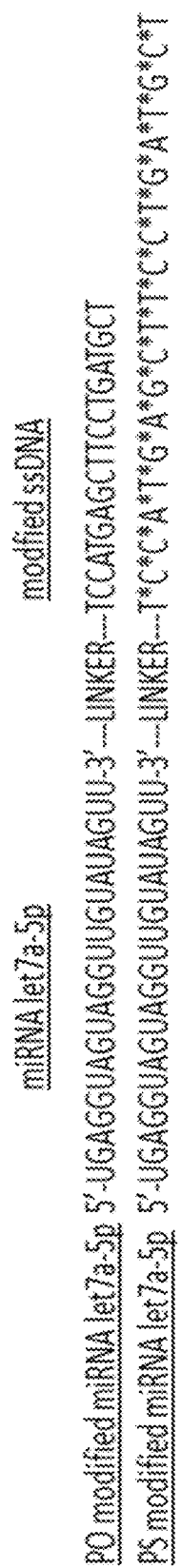
FIG. 3: Modified let7a-5p miRNA (SEQ ID NO:2). A nucleic acid conjugate comprising a stretch of non-cell penetrating let7a-5p miRNA, a phosphorothioated nucleic acid, and a chemical linker attaching the phosphorothioated nucleic acid to the let7a-5p miRNA, is shown. To enhance intracellular delivery, the non-cell penetrating let7a-5p miRNA sequence was extended at its 3'-end by a chemical linker followed by a 20meric ssDNA stretch. It is critical that the sugar-phosphate backbone is phosphorothioated (PS; bottom sequence of FIG. 3) indicated by (*) to achieve cellular internalization; a control miRNA was used without phosphorothioation (phosphodiester, PO; top sequence of FIG. 3).
Figures 5, 6A:
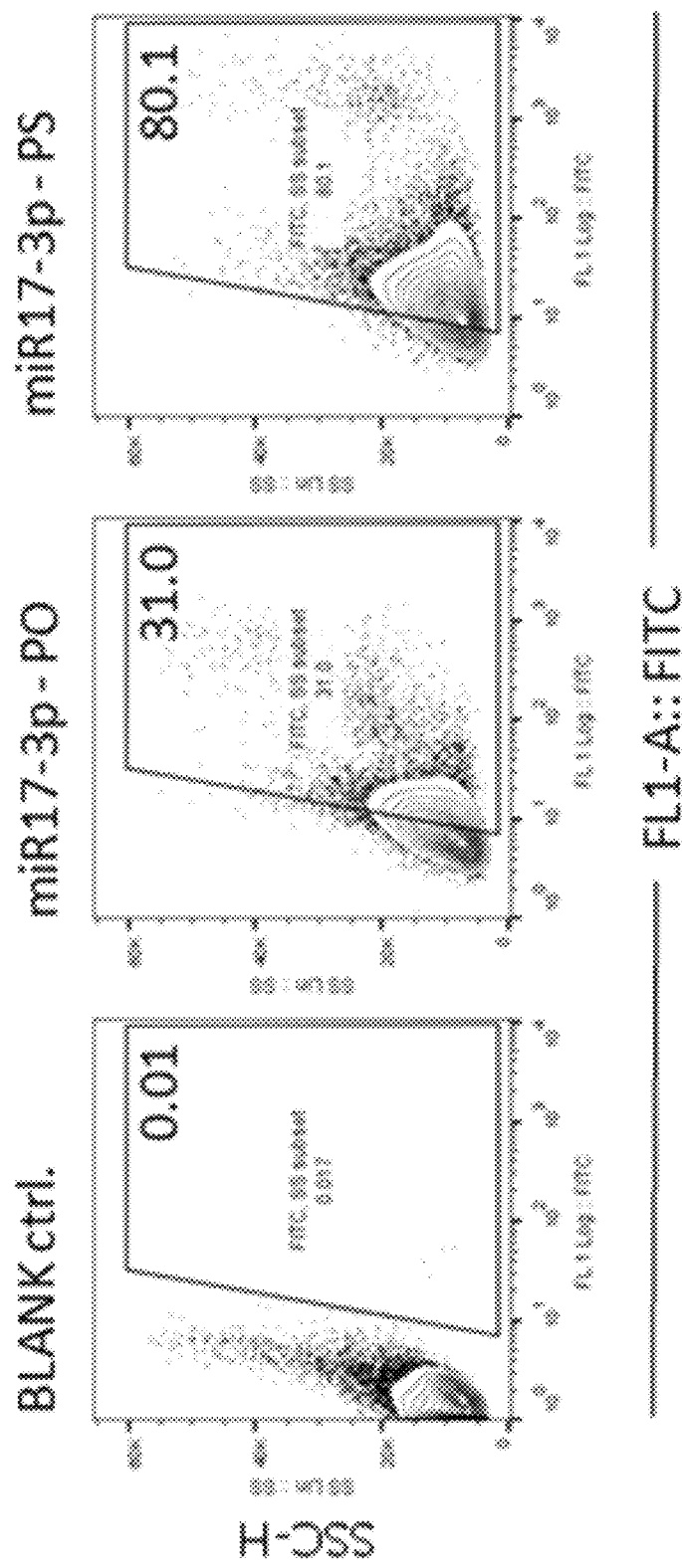
FIG. 5: Modified miR17-3p miRNA (SEQ ID NO:3). A nucleic acid conjugate comprising a stretch of non-cell penetrating miR17-3p miRNA, a phosphorothioated nucleic acid, and a chemical linker attaching the phosphorothioated nucleic acid to the miR17-3p miRNA, is shown. To enhance intracellular delivery, the miR17-3p miRNA was extended at its 3'-end by a chemical linker followed by a 20meric ssDNA stretch. It is critical that the sugar-phosphate backbone is phosphorothioated (PS; bottom sequence of FIG. 5) indicated by (*) to achieve cellular internalization; a control miRNA was used without phosphorothioation (phosphodiester, PO; top sequence of FIG. 5).
FIGS. 6A-6C: miR17-3p miRNA (SEQ ID NO:3) intracellular delivery and reduced STAT3 target gene expression.
Figure 7:
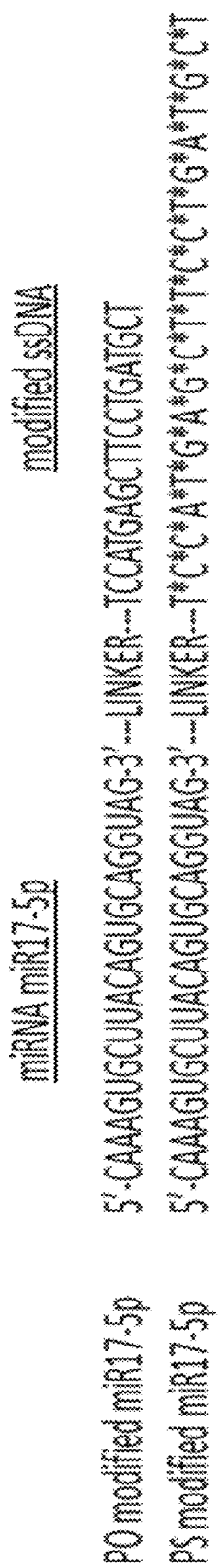
FIG. 7: Modified miR17-5p miRNA (SEQ ID NO:4). A nucleic acid conjugate comprising a stretch of non-cell penetrating miR17-5p miRNA, a phosphorothioated nucleic acid, and a chemical linker attaching the phosphorothioated nucleic acid to the miR17-5p miRNA, is shown. To enhance intracellular delivery, the miR17-5p miRNA was extended at its 3'-end by a chemical linker followed by a 20meric ssDNA stretch. It is critical that the sugar-phosphate backbone is phosphorothioated (PS; bottom sequence of FIG. 7) indicated by (*) to achieve cellular internalization; a control miRNA was used without phosphorothioation (phosphodiester, PO; top sequence of FIG. 7).

Applicants modified naturally occurring miRNAs, for example, 1et7a-3p (SEQ ID NO:1) (FIG. 1), 1et7a-5p (SEQ ID NO:2) (FIG. 3), miR17-3p (SEQ ID NO:3) (FIG. 5), miR17-5p (SEQ ID NO:4) (FIG. 7), and miR218-5p (SEQ ID NO:5) (FIG. 9) by attaching a phosphorothioated ssDNA (PS) 20meric oligo to the 3' end of the miRNAs via a chemical linker. Examples of a phosphorothioated ssDNA (PS) 20meric oligo include, but are not limited to, SEQ ID NO:6 (TCCATGAGCTTCCTGATGCT) and SEQ ID NO:7 (AGCATCAGGAAGCTCATGGA).

Applicants designed that the modification by ssDNA oligo avoids any C/G or G/C motifs, because it is known that CpG oligodeoxynucleotides (CpG-ODN) involve undesired Toll-like receptor (TLR) engagement and subsequent intracellular signaling. Applicants used an alkyl chain harboring a fluorophore as a linker to track the conjugate molecule.

Figure 2B:
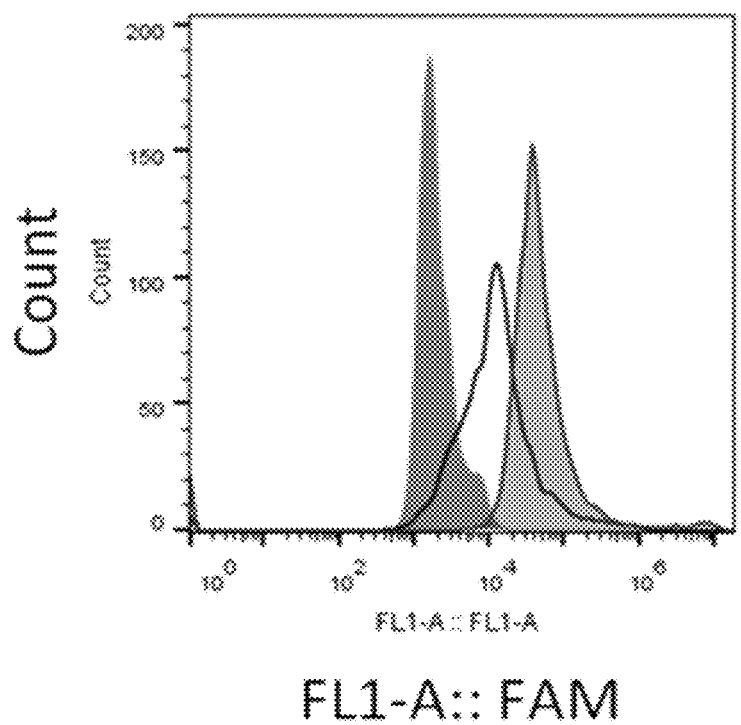
Figure 2C:
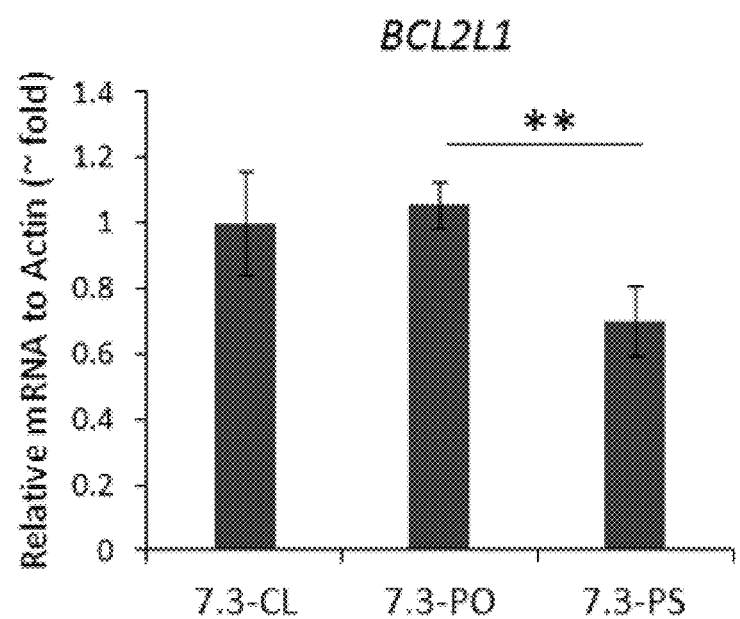
Figure 4A:
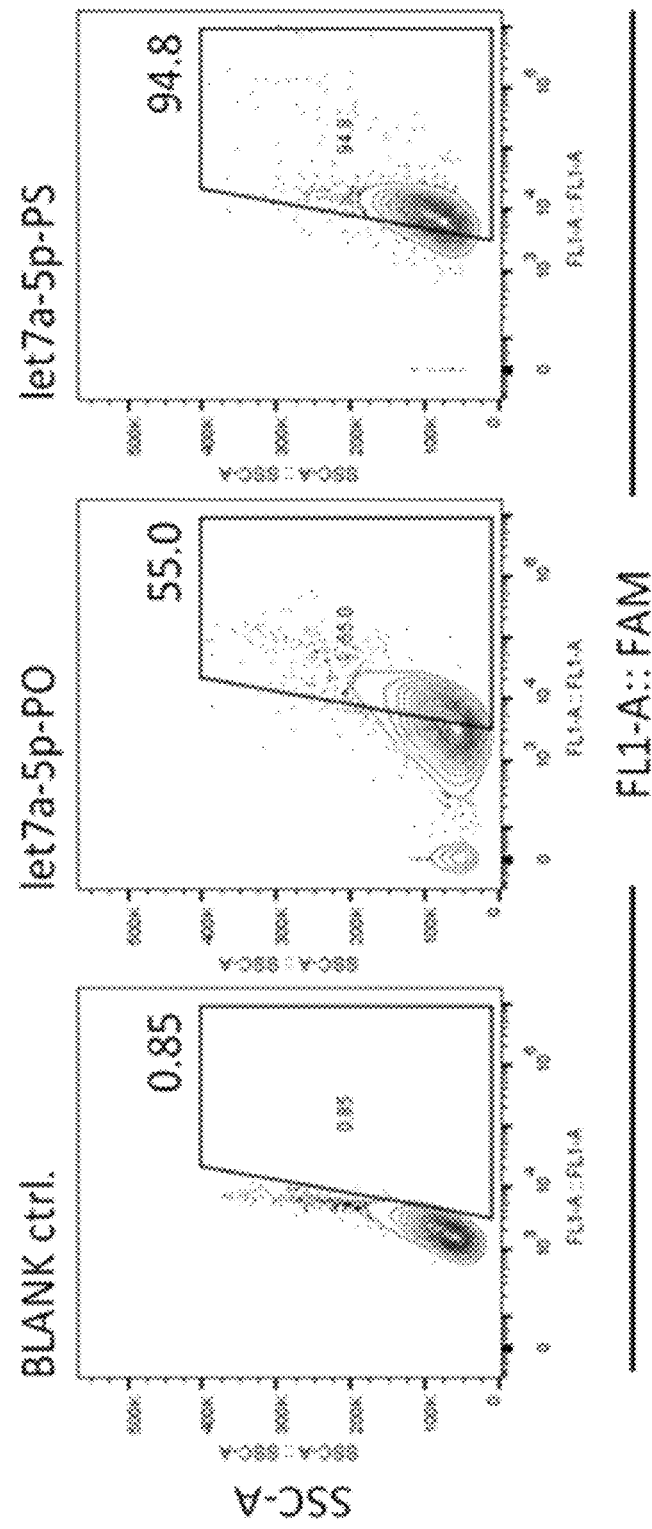
FIGS. 4A-4C: Intracellular delivery of let7a-5p miRNA (SEQ ID NO:2) and reduced STAT3 target gene expression.
Figure 4B:
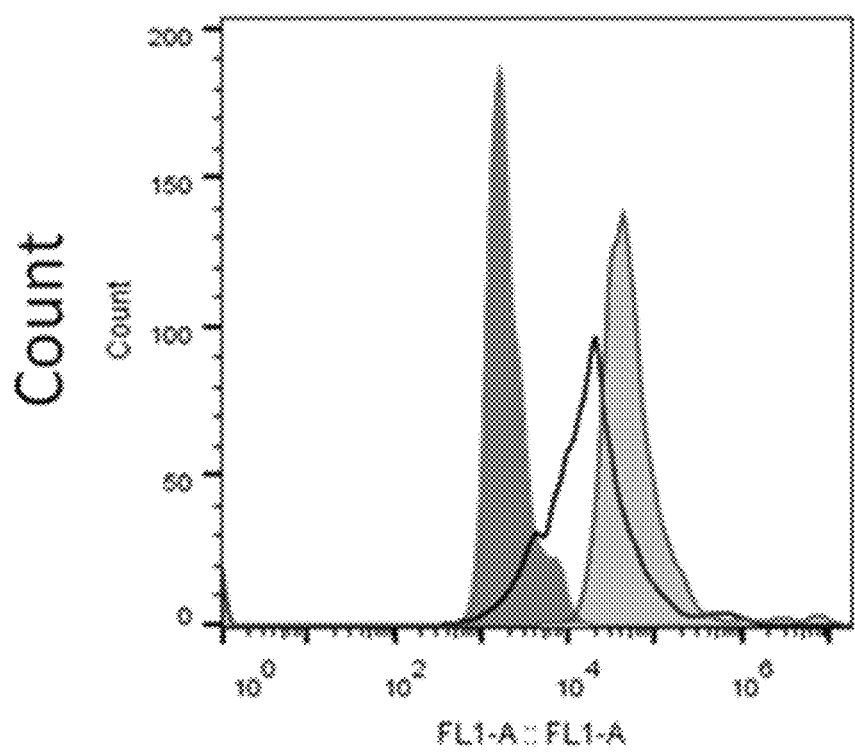
Figure 4C:
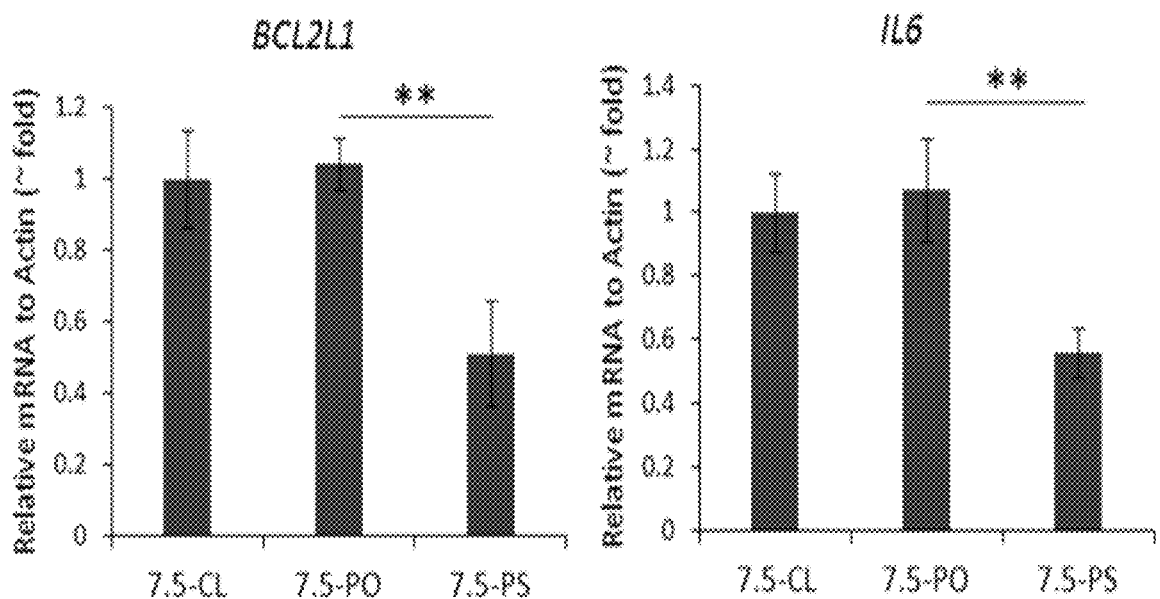
Figure 6B:
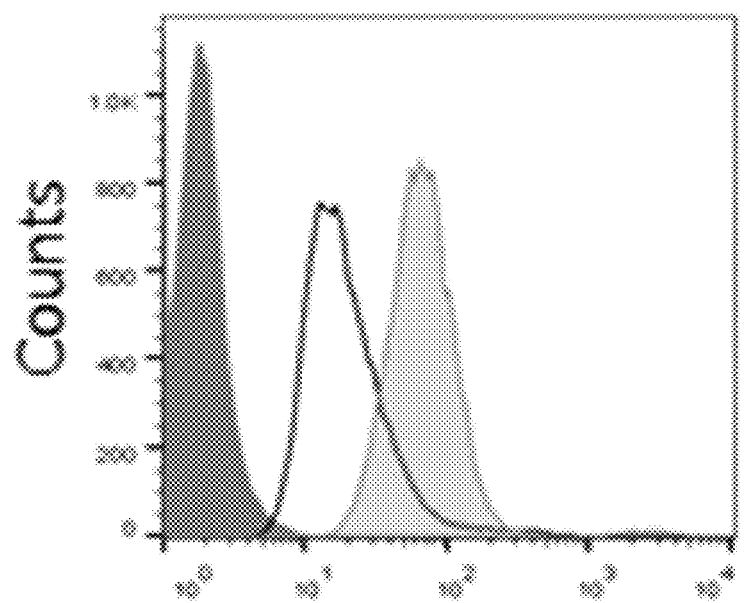
Figure 6C:
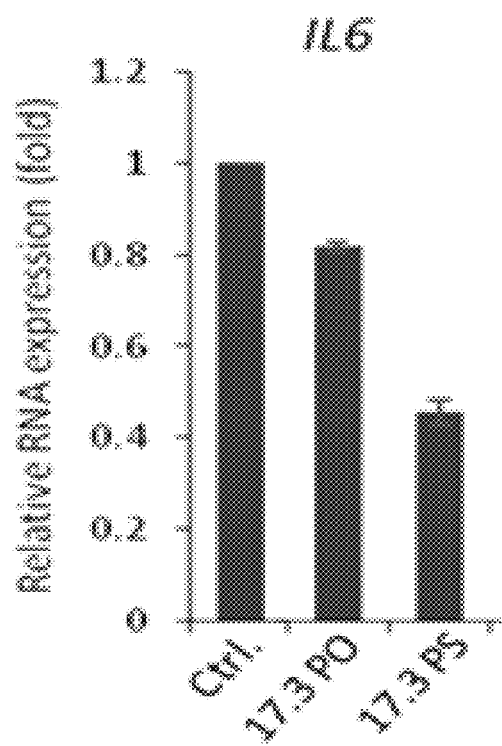
Figure 8A:
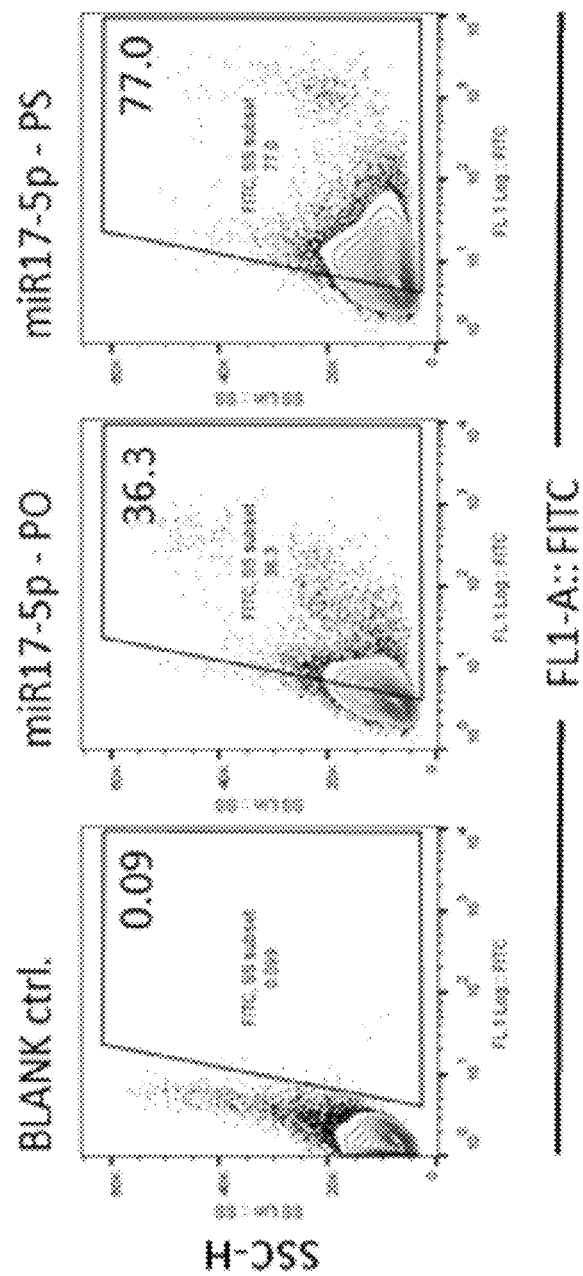
FIGS. 8A-8C: miR17-5p miRNA (SEQ ID NO:4) intracellular delivery and reduced STAT3 target gene expression.
Figure 8B:
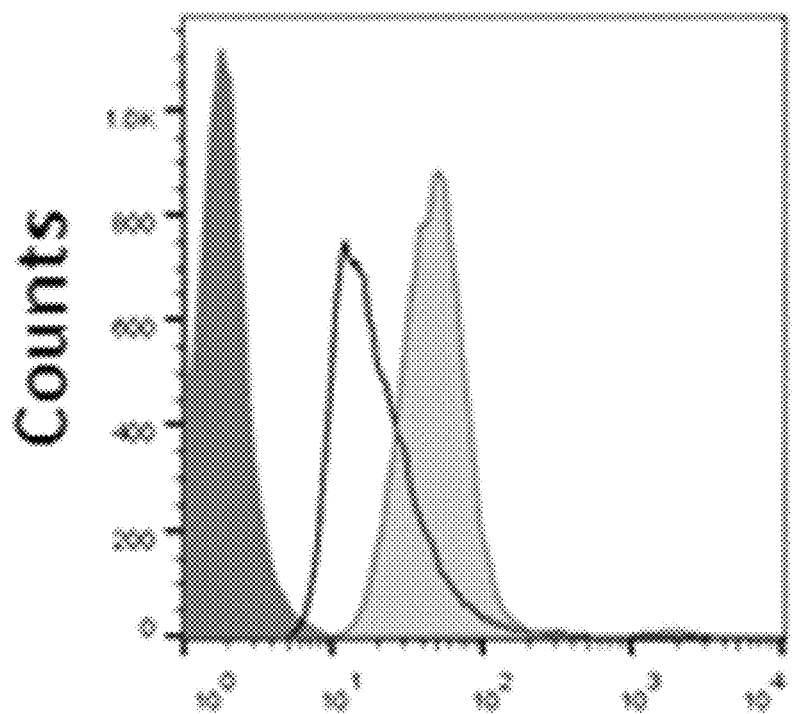
Figure 8C:
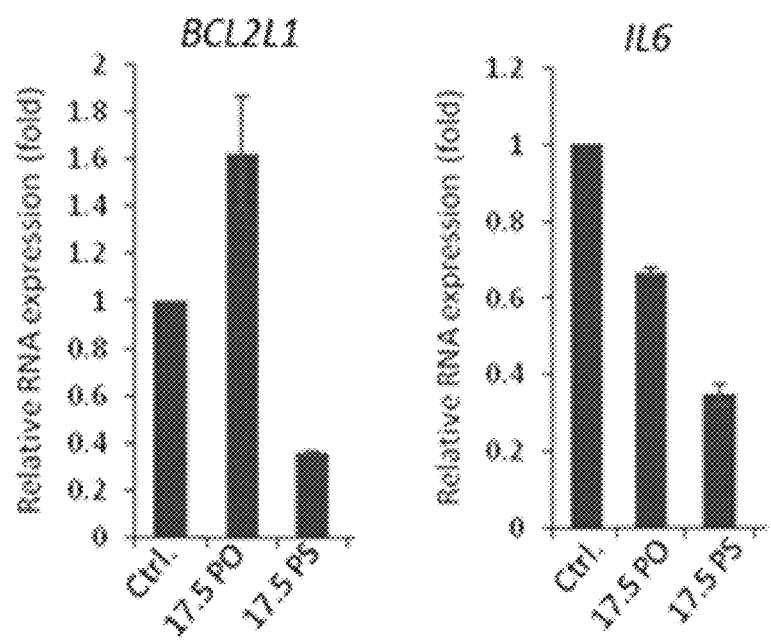
Figure 10B:
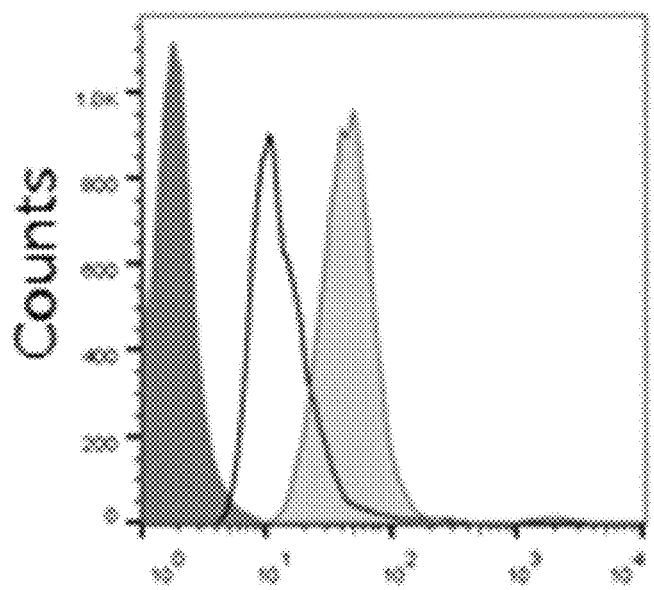
Figure 10C:
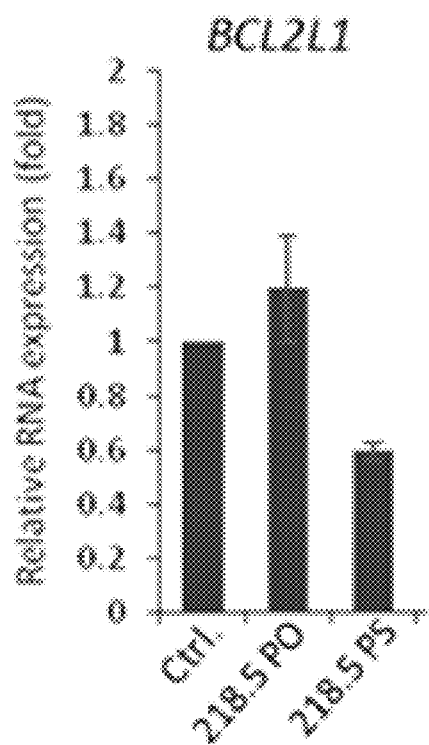

Example 2: Modified MiRNA Elongated with Phosphorothioated SSDNA Oligonucleotides Undergo Cellular Internalization Once miRNAs were modified by elongation and fluorescently marked to enable intracellular tracking of modified miRNAs, Applicants assessed cellular internalization of PS-modified miRNAs by flow cytometry including PO-modified miRNA as negative non-internalizing controls. Human multiple myeloma cells MM.1S were incubated either for 30 min or for 48 hrs with modified miRNA as indicated and analyzed by flow cytometry to assess cellular load of cells with modified miRNA. For modified 1et7a-3p miRNA (FIGS. 2A and 2B) and modified 1et7a-5p miRNA (FIGS. 4A and 4B), 10 µg/ml was used for both 30 min and 48 hr incubation. For miR17-3p miRNA (FIGS. 6A and 6B), modified miR17-5p miRNA (FIGS. 8A and 8B) and modified miR218-5p miRNA (FIGS. 10A and 10B), 20 µg/ml was used for 30 min incubation and 10 µg/ml was used for 48 hr incubation, respectively.

Example 3: Modified MiRNA Elongated with Phosphorothioated SSDNA Oligonucleotides Reducing Stat3 Target Gene Expression Human multiple myeloma cancer cells are known to undergo increased cell division through IL-6-triggered STAT3 signaling. Numerous studies have shown that 1et7a-3p miRNA (SEQ ID NO:1), 1et7a-5p miRNA (SEQ ID NO:2), miR17-3p miRNA (SEQ ID NO:3), miR17-5p miRNA (SEQ ID NO:4), or miR218-5p miRNA (SEQ ID NO:5) inhibits the activity of transcription factor Signal Transducer and Activator of Transcription 3 (STAT3). Human multiple myeloma cells MM.1S were incubated for 48 hrs daily with 10 µg/ml modified miRNA as indicated and expression of the STAT3 target genes was analyzed by RT-PCR. As shown in FIGS. 2C, 4C, 6C, 8C and 10C, incubation with PS-modified 1et7a-3p miRNA (SEQ ID NO:1), 1et7a-5p miRNA (SEQ ID NO:2), miR17-3p miRNA (SEQ ID NO:3), miR17-5p miRNA (SEQ ID NO:4), or miR218-5p miRNA (SEQ ID NO:5) inhibited expression of STAT3 target genes, for example, oncogenic Bcl-xL and/or
IL-6 genes.

Example 4: Production of Cell Internalizing Nucleic Acid Compounds Via Covalent Linkage to Phosphorothioated Single-Stranded Abasic Sugar-Phosphate Backbone Polymers miRNAs with naturally occurring sequences were fused covalently to a phosphorothioated single-stranded abasic sugar-phosphate backbone (PS) 20meric polymer to facilitate cellular internalization targeting intracellular molecular targets. A non-phosphorothioated, phosphodiester single-stranded abasic sugar-phosphate backbone polymer (PO) extension of the miRNAs was employed as a non-internalizing control.

Figures 11A, 11B:
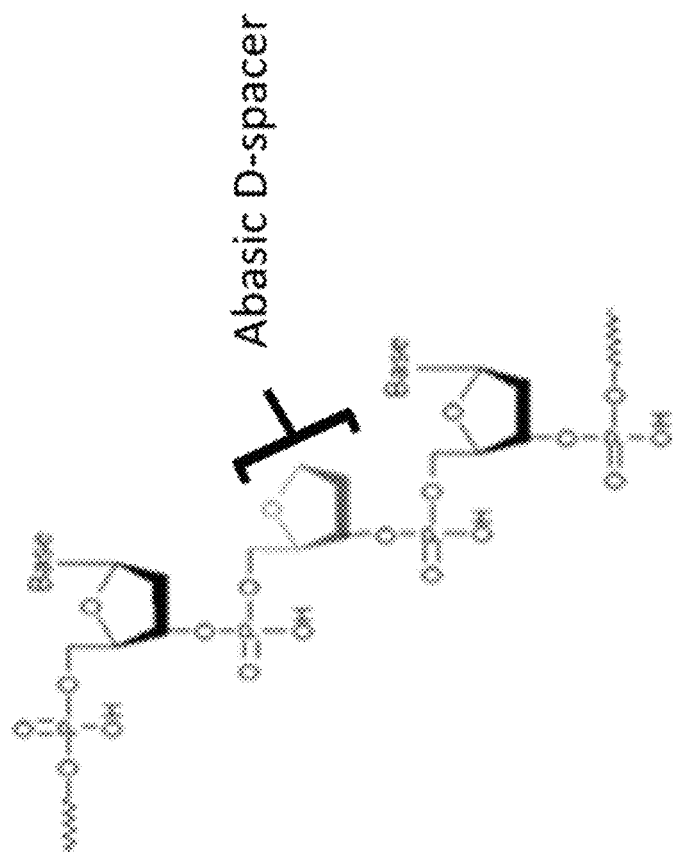
FIG. 11A-11B: Polymer-modified 1et7a-5p miRNA (SEQ ID NO:2).

Applicants modified naturally occurring miRNAs, for example, 1et7a-5p (SEQ ID NO:2) by attaching a phosphorothioated single-stranded abasic sugar-phosphate backbone (PS) 20meric polymer to the 3' end of the miRNAs via a chemical linker (FIG. 11A). Applicants designed the modification based on that phosphorothioated ssDNA oligo enables successful intracellular delivery, but bases (nucleic acids) may not be required to facilitate intracellular delivery of the conjugate and thus may be excluded. FIG. 11B schematically shows the abasic sugar-phosphate module (referred as "D") lacking a base (a nucleic acid) in comparison to basic "spacers." Applicants used an alkyl chain harboring a fluorophore as a linker to track the conjugate molecule.

Figure 12A:
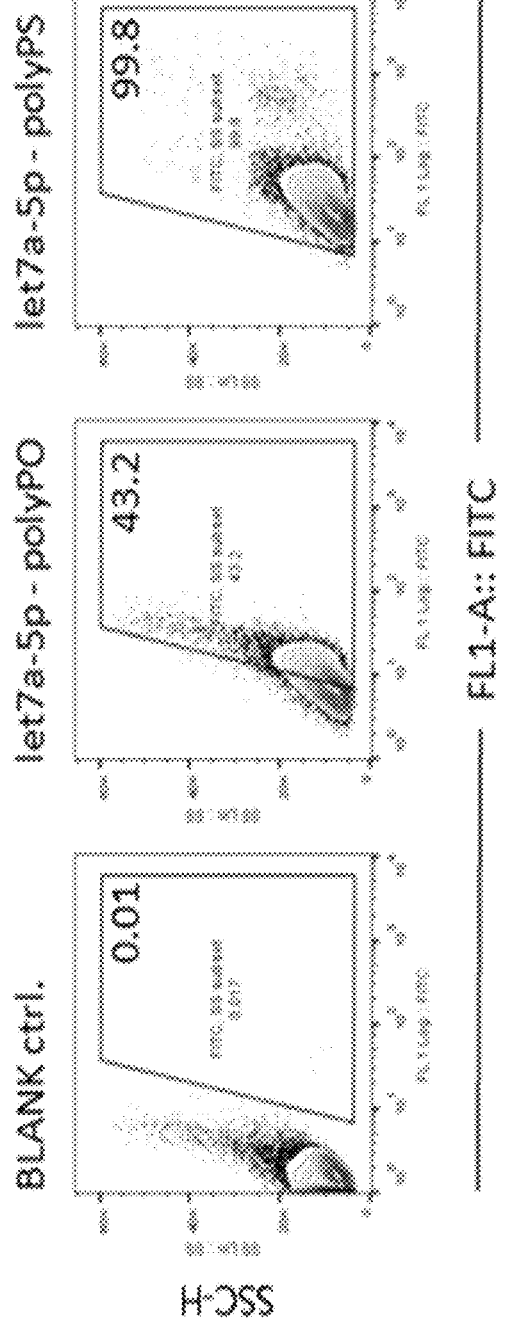
FIGS. 12A-12B: Polymer-modified 1et7a-5p miRNA (SEQ ID NO:2) intracellular delivery and reduced STAT3 target gene expression.

Example 5: Modified MiRNA Elongated with Phosphorothioated Single-Stranded Abasic Sugar-Phosphate Backbone Polymers Undergo Cellular Internalization Once miRNAs were modified by elongation and fluorescently marked to enable intracellular tracking of modified miRNAs, Applicants assessed cellular internalization of PS polymer-modified miRNAs by flow cytometry including PO polymer-modified miRNA as negative non-internalizing controls. Human multiple myeloma cells MM.1S were incubated for 30 min (FIG. 12A) with 20 µg/ml polymer-modified 1et7a-5p miRNA as indicated and analyzed by flow cytometry to assess cellular load of cells with modified miRNA.

Figure 12B:
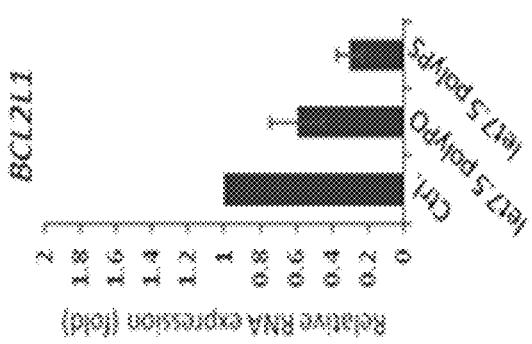

Example 6: Modified MiRNA Elongated with Phosphorothioated Single-Stranded Abasic Sugar-Phosphate Backbone Polymers Reducing Stat3 Target Gene Expression Human multiple myeloma cancer cells are known to undergo increased cell division through IL-6-triggered STAT3 signaling. Numerous studies have shown that 1et7a-5p miRNA (SEQ ID NO:2) inhibits the activity of Signal Transducer and Activator of Transcription 3 (STAT3). Human multiple myeloma cells MM.1S were incubated for 48 hrs daily with 10 µg/ml polymer-modified 1et7a-5p miRNA as indicated and expression of the STAT3 target gene, oncogenic Bcl-xL gene, was analyzed by RT-PCR. As shown in FIG. 12B, incubation with PS polymer-modified 1et7a-5p miRNA inhibited expression of Bcl-xL gene.

REFERENCES

Herrmann, A., Nachaev, S., Lahtz, C., Armstrong, B., Kowolik, C., Kortylewski, M., Jove, R., and Hua, Y. (2014). STAT3 nuclear egress requires exportin 7 via engaging lysine acetylation. MOJ Cell Sci Report 1(1): 00004. DOI: 10.15406/mojcsr.2014.01.00004.

P Embodiments

P Embodiment 1. A cell penetrating nucleic acid conjugate comprising:
(i) a non-cell penetrating ribonucleic acid compound comprising the sequence of SEQ ID NO:1, SEQ ID NO:2, SEQ ID NO:3, SEQ ID NO:4 or SEQ ID NO:5;
(ii) a phosphorothioate polymer; and
(iii) a chemical linker attaching said phosphorothioate polymer to the 3' end of said non-cell penetrating ribonucleic acid compound;
wherein said phosphorothioate polymer enhances intracellular delivery of the non-cell penetrating nucleic acid compound.

P Embodiment 2. The conjugate of P Embodiment 1, wherein said non-cell penetrating ribonucleic acid compound is a micro RNA (miRNA).

P Embodiment 3. The conjugate of P Embodiment 1 or 2, wherein said non-cell penetrating ribonucleic acid compound is about 10, 20, 30, 40, 50, 60, 70, 80, 90 or more residues in length.

P Embodiment 4. The conjugate of any one of P Embodiments 1-3, wherein said non-cell penetrating ribonucleic acid compound is from about 20 to about 30 residues in length.

P Embodiment 5. The conjugate of any one of P Embodiments 1-4, wherein said non-cell penetrating ribonucleic acid compound is from about 20 to about 25 residues in length.

P Embodiment 6. The conjugate of any one of P Embodiments 1-5, wherein said non-cell penetrating ribonucleic acid compound is 21, 22 or 23 residues in length.

P Embodiment 7. The conjugate of any one of P Embodiments 1-6, wherein said phosphorothioate polymer is a phosphorothioate nucleic acid or an abasic sugar-phosphorothioated polymer.

P Embodiment 8. The conjugate of any one of P Embodiments 1-7, wherein said phosphorothioate polymer is a phosphorothioate deoxyribonucleic acid.

P Embodiment 9. The conjugate of any one of P Embodiments 1-8, wherein said phosphorothioate polymer is about 10, 20, 30, 40, 50, 60, 70, 80, 90, 100 or more residues in length.

P Embodiment 10. The conjugate of any one of P Embodiments 1-9, wherein said phosphorothioate polymer is from about 10 to about 30 residues in length.

P Embodiment 11. The conjugate of any one of P Embodiments 1-10, wherein said phosphorothioate polymer is about 20 residues in length.

P Embodiment 12. The conjugate of any one of P Embodiments 1-11, wherein said phosphorothioate polymer comprises the sequence of SEQ ID NO:6 or SEQ ID NO:7.

P Embodiment 13. The conjugate of any one of P Embodiments 1-12, wherein said phosphorothioate polymer is single-stranded.

P Embodiment 14. The conjugate of any one of P Embodiments 1-13, wherein said chemical linker is a covalent linker.

P Embodiment 15. The conjugate of any one of P Embodiments 1-14, wherein said chemical linker is a non-immunogenic linker.

P Embodiment 16. The conjugate of any one of P Embodiments 1-15, wherein said conjugate further comprises a detectable moiety.

P Embodiment 17. The conjugate of P Embodiment 16, wherein said detectable moiety is attached to said non-cell penetrating ribonucleic acid compound.

P Embodiment 18. The conjugate of P Embodiment 16, wherein said detectable moiety is attached to said phosphorothioate polymer.

P Embodiment 19. The conjugate of any one of P Embodiments 1-18, wherein said non-cell penetrating ribonucleic acid compound inhibits STAT3 activity relative to a standard control.

P Embodiment 20. The conjugate of any one of P Embodiments 1-19, wherein said non-cell penetrating ribonucleic acid compound inhibits expression of a STAT3 target gene relative to a standard control.

P Embodiment 21. The conjugate of P Embodiment 20, wherein said STAT3 target gene is an oncogene.

P Embodiment 22. The conjugate of P Embodiment 20, wherein said STAT3 target gene is Bcl-xL or IL-6.

P Embodiment 23. A cell comprising a cell penetrating nucleic acid conjugate of any one of P Embodiments 1-22.

P Embodiment 24. A pharmaceutical composition comprising a cell penetrating nucleic acid conjugate of any one of P Embodiments 1-22 and a pharmaceutically acceptable carrier.

P Embodiment 25. A method of treating cancer in a subject in need thereof, said method comprising administering to said subject a therapeutically effective amount of a cell penetrating nucleic acid conjugate of any one of P Embodiments 1-22, thereby treating said cancer in said subject.

P Embodiment 26. The method of P Embodiment 25, wherein said cancer is breast cancer, prostate cancer, ovarian cancer, brain cancer, pancreatic cancer, melanoma, colon cancer, gastric cancer, head-and-neck cancer, liver cancer, lung cancer, cervical cancer, sarcoma, leukemia, lymphoma, multiple myeloma.

P Embodiment 27. The method of P Embodiment 26, said method comprising decreasing in said subject an expression level of BIRC5 or Bcl-xL relative to a standard control.

P Embodiment 28. A method of increasing expression of p53 in a cancer cell, said method comprising contacting a cancer cell with an effective amount of a cell penetrating nucleic acid conjugate of any one of P Embodiments 1-22, thereby increasing expression of p53 in said cancer cell.

P Embodiment 29. A method of inhibiting tumor vascularization in a subject in need thereof, said method comprising administering to said subject a therapeutically effective amount of a cell penetrating nucleic acid conjugate of any one of P Embodiments 1-22, thereby inhibiting tumor vascularization in said subject.

P Embodiment 30. A method of treating an inflammatory disease in a subject in need thereof, said method comprising administering to said subject a therapeutically effective amount of a cell penetrating nucleic acid conjugate of any one of P Embodiments 1-22, thereby treating an inflammatory disease in said subject.

P Embodiment 31. The method of P Embodiment 30, said method comprising decreasing in said subject an expression level of FGA, IL1B or SERPINA3 relative to a standard control.

P Embodiment 32. A method of treating pain in a subject in need thereof, said method comprising administering to said subject a therapeutically effective amount of a cell penetrating nucleic acid conjugate of any one of P Embodiments 1-22, thereby treating pain in said subject.

P Embodiment 33. The method of P Embodiment 32, said method comprising decreasing in said subject an expression level of PTGS1, PTGS2, CALCA or SST relative to a standard control.

P Embodiment 34. A method of inhibiting IL-6 signaling in a cell, said method comprising contacting a cell with an effective amount of a cell penetrating nucleic acid conjugate of any one of P Embodiments 1-22, thereby inhibiting IL-6 signaling in said cell.

P Embodiment 35. A method of delivering a non-cell penetrating nucleic acid into a cell, said method comprising contacting a cell with a cell penetrating nucleic acid conjugate of any one of P Embodiments 1-22, thereby delivering said non-cell penetrating nucleic acid into said cell.

INFORMAL SEQUENCE LISTING let7a-3p miRNA (SEQ ID NO: 1):
CUAUACAAUCUACUGUCUUUC let7a-5p miRNA (SEQ ID NO: 2):
UGAGGUAGUAGGUUGUAUAGUU miR17-3p miRNA (SEQ ID NO: 3):
ACUGCAGUGAAGGCACUUGUAG miR17-5p miRNA (SEQ ID NO: 4):
CAAAGUGCUUACAGUGCAGGUAG miR218-5p miRNA (SEQ ID NO: 5):
UUGUGCUUGAUCUAACCAUGU phosphorothioate polymer (SEQ ID NO: 6):
TCCATGAGCTTCCTGATGCT phosphorothioate polymer (SEQ ID NO: 7):
AGCATCAGGAAGCTCATGGA STAT3 polypeptide (SEQ ID NO: 8):
MAQWNQLQQLDTRYLEQLHQLYSDSFPMELRQFLAPWIESQDWAYAAS

KESHATLVFHNLLGEIDQQYSRFLQESNVLYQHNLRRIKQFLQSRYLE

KPMEIARIVARCLWEESRLLQTAATAAQQGGQANHPTAAVVTEKQQML

EQHLQDVRKRVQDLEQKMKVVENLQDDFDFNYKTLKSQGDMQDLNGNN

QSVTRQKMQQLEQMLTALDQMRRSIVSELAGLLSAMEYVQKTLTDEEL

ADWKRRQQIACIGGPPNICLDRLENWITSLAESQLQTRQQIKKLEELQ

QKVSYKGDPIVQHRPMLEERIVELFRNLMKSAFVVERQPCMPMHPDRP

LVIKTGVQFTTKVRLLVKFPELNYQLKIKVCIDKDSGDVAALRGSRKF

NILGTNTKVMNMEESNNGSLSAEFKHLTLREQRCGNGGRANCDASLIV

TEELHLITFETEVYHQGLKIDLETHSLPVVVISNICQMPNAWASILWY

NMLTNNPKNVNFFTKPPIGTWDQVAEVLSWQFSSTTKRGLSIEQLTTL

AEKLLGPGVNYSGCQITWAKFCKENMAGKGFSFWVWLDNIIDLVKKYI

LALWNEGYIMGFISKERERAILSTKPPGTFLLRFSESSKEGGVTFTWV

EKDISGKTQIQSVEPYTKQQLNNMSFAEIIMGYKIMDATNILVSPLVY

LYPDIPKEEAFGKYCRPESQEHPEADPGSAAPYLKTKFICVTPTTCSN

TIDLPMSPRTLDSLMQFGNNGEGAEPSAGGQFESLTFDMELTSECATS

PM

What is claimed is:

1. A cell penetrating nucleic acid conjugate comprising:
   (i) a non-cell penetrating ribonucleic acid compound comprising the sequence of SEQ ID NO:1, SEQ ID NO:2, SEQ ID NO:3, SEQ ID NO:4 or SEQ ID NO:5;
   (ii) a phosphorothioate polymer; and
   (iii) a chemical linker attaching said phosphorothioate polymer to the 3' end of said non-cell penetrating ribonucleic acid compound;
   wherein said phosphorothioate polymer enhances intracellular delivery of the non-cell penetrating nucleic acid compound and wherein said non-cell penetrating ribonucleic acid compound is a non-phosphorothioated ribonucleic acid.

2. The conjugate of claim 1, wherein said non-cell penetrating ribonucleic acid compound is a micro RNA (miRNA).

3. The conjugate of claim 1, wherein said non-cell penetrating ribonucleic acid compound is from about 20 to about 30 residues in length.

4. The conjugate of claim 1, wherein said phosphorothioate polymer is a phosphorothioate deoxyribonucleic acid.

5. The conjugate of claim 1, wherein said phosphorothioate polymer is from about 10 to about 30 residues in length.

6. The conjugate of claim 1, wherein said phosphorothioate polymer comprises the sequence of SEQ ID NO:6 or SEQ ID NO:7.

7. The conjugate of claim 1, wherein said phosphorothioate polymer is single-stranded.

8. The conjugate of claim 1, wherein said chemical linker is a covalent linker.

9. The conjugate of claim 1, wherein said conjugate further comprises a detectable moiety.

10. The conjugate of claim 1, wherein said non-cell penetrating ribonucleic acid compound inhibits STAT3 activity relative to a standard control.

11. The conjugate of claims 1, wherein said non-cell penetrating ribonucleic acid compound inhibits expression of a STAT3 target gene relative to a standard control.

12. A cell comprising a cell penetrating nucleic acid conjugate of claim 1.

13. A pharmaceutical composition comprising a cell penetrating nucleic acid conjugate claim 1 and a pharmaceutically acceptable carrier.

14. A method of treating multiple myeloma in a subject in need thereof, said method comprising administering to said subject a therapeutically effective amount of a cell penetrating nucleic acid conjugate of claim 1, thereby treating said cancer in said subject.

15. A method of inhibiting IL-6 signaling in a cell, said method comprising contacting a cell with an effective amount of a cell penetrating nucleic acid conjugate of claim 1, thereby inhibiting IL-6 signaling in said cell.

16. A method of delivering a non-cell penetrating nucleic acid into a cell, said method comprising contacting a cell with a cell penetrating nucleic acid conjugate of claim 1, thereby delivering said non-cell penetrating nucleic acid into said cell.

* * * * *

SEQUENCE LISTING

<160> NUMBER OF SEQ ID NOS: 8

<210> SEQ ID NO 1
<211> LENGTH: 21
<212> TYPE: RNA
<213> ORGANISM: Artificial sequence

```
<220> FEATURE:
<223> OTHER INFORMATION: Synthetic polynucleotide
<220> FEATURE:
<221> NAME/KEY: misc_feature
<223> OTHER INFORMATION: let7a-3p miRNA

<400> SEQUENCE: 1
cuauacaauc uacugucuuu c                                              21

<210> SEQ ID NO 2
<211> LENGTH: 22
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: let7a-5p miRNA

<400> SEQUENCE: 2
ugagguagua gguuguauag uu                                             22

<210> SEQ ID NO 3
<211> LENGTH: 22
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR17-3p miRNA

<400> SEQUENCE: 3
acugcaguga aggcacuugu ag                                             22

<210> SEQ ID NO 4
<211> LENGTH: 23
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR17-5p miRNA

<400> SEQUENCE: 4
caaagugcuu acagugcagg uag                                            23

<210> SEQ ID NO 5
<211> LENGTH: 21
<212> TYPE: RNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: miR218-5p miRNA

<400> SEQUENCE: 5
uugugcuuga ucuaaccaug u                                              21

<210> SEQ ID NO 6
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
```

<223> OTHER INFORMATION: phosphorothioate polymer

<400> SEQUENCE: 6
tccatgagct tcctgatgct                                                    20

<210> SEQ ID NO 7
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: phosphorothioate polymer

<400> SEQUENCE: 7
agcatcagga agctcatgga                                                    20

<210> SEQ ID NO 8
<211> LENGTH: 770
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: STAT3 polypeptide

<400> SEQUENCE: 8

```
Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
        35                  40                  45

Lys Glu Ser His Ala Thr Leu Val Phe His Asn Leu Leu Gly Glu Ile
    50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
                85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
        115                 120                 125

Ala Asn His Pro Thr Ala Ala Val Val Thr Glu Lys Gln Gln Met Leu
    130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
    210                 215                 220

Leu Ser Ala Met Glu Tyr Val Gln Lys Thr Leu Thr Asp Glu Glu Leu
225                 230                 235                 240
```

```
Ala Asp Trp Lys Arg Arg Gln Gln Ile Ala Cys Ile Gly Gly Pro Pro
            245                 250                 255
Asn Ile Cys Leu Asp Arg Leu Glu Asn Trp Ile Thr Ser Leu Ala Glu
        260                 265                 270
Ser Gln Leu Gln Thr Arg Gln Gln Ile Lys Lys Leu Glu Glu Leu Gln
    275                 280                 285
Gln Lys Val Ser Tyr Lys Gly Asp Pro Ile Val Gln His Arg Pro Met
290                 295                 300
Leu Glu Glu Arg Ile Val Glu Leu Phe Arg Asn Leu Met Lys Ser Ala
305                 310                 315                 320
Phe Val Val Glu Arg Gln Pro Cys Met Pro Met His Pro Asp Arg Pro
                325                 330                 335
Leu Val Ile Lys Thr Gly Val Gln Phe Thr Thr Lys Val Arg Leu Leu
            340                 345                 350
Val Lys Phe Pro Glu Leu Asn Tyr Gln Leu Lys Ile Lys Val Cys Ile
        355                 360                 365
Asp Lys Asp Ser Gly Asp Val Ala Ala Leu Arg Gly Ser Arg Lys Phe
    370                 375                 380
Asn Ile Leu Gly Thr Asn Thr Lys Val Met Asn Met Glu Glu Ser Asn
385                 390                 395                 400
Asn Gly Ser Leu Ser Ala Glu Phe Lys His Leu Thr Leu Arg Glu Gln
                405                 410                 415
Arg Cys Gly Asn Gly Gly Arg Ala Asn Cys Asp Ala Ser Leu Ile Val
            420                 425                 430
Thr Glu Glu Leu His Leu Ile Thr Phe Glu Thr Glu Val Tyr His Gln
        435                 440                 445
Gly Leu Lys Ile Asp Leu Glu Thr His Ser Leu Pro Val Val Val Ile
    450                 455                 460
Ser Asn Ile Cys Gln Met Pro Asn Ala Trp Ala Ser Ile Leu Trp Tyr
465                 470                 475                 480
Asn Met Leu Thr Asn Asn Pro Lys Asn Val Asn Phe Phe Thr Lys Pro
                485                 490                 495
Pro Ile Gly Thr Trp Asp Gln Val Ala Glu Val Leu Ser Trp Gln Phe
            500                 505                 510
Ser Ser Thr Thr Lys Arg Gly Leu Ser Ile Glu Gln Leu Thr Thr Leu
        515                 520                 525
Ala Glu Lys Leu Leu Gly Pro Gly Val Asn Tyr Ser Gly Cys Gln Ile
    530                 535                 540
Thr Trp Ala Lys Phe Cys Lys Glu Asn Met Ala Gly Lys Gly Phe Ser
545                 550                 555                 560
Phe Trp Val Trp Leu Asp Asn Ile Ile Asp Leu Val Lys Lys Tyr Ile
                565                 570                 575
Leu Ala Leu Trp Asn Glu Gly Tyr Ile Met Gly Phe Ile Ser Lys Glu
            580                 585                 590
Arg Glu Arg Ala Ile Leu Ser Thr Lys Pro Pro Gly Thr Phe Leu Leu
        595                 600                 605
Arg Phe Ser Glu Ser Ser Lys Glu Gly Gly Val Thr Phe Thr Trp Val
    610                 615                 620
Glu Lys Asp Ile Ser Gly Lys Thr Gln Ile Gln Ser Val Glu Pro Tyr
625                 630                 635                 640
Thr Lys Gln Gln Leu Asn Asn Met Ser Phe Ala Glu Ile Ile Met Gly
                645                 650                 655
Tyr Lys Ile Met Asp Ala Thr Asn Ile Leu Val Ser Pro Leu Val Tyr
```

-continued

```
                660                 665                 670
Leu Tyr Pro Asp Ile Pro Lys Glu Glu Ala Phe Gly Lys Tyr Cys Arg
        675                 680                 685

Pro Glu Ser Gln Glu His Pro Glu Ala Asp Pro Gly Ser Ala Ala Pro
        690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
                740                 745                 750

Glu Ser Leu Thr Phe Asp Met Glu Leu Thr Ser Glu Cys Ala Thr Ser
        755                 760                 765

Pro Met
    770
```